US012723913B2

(12) United States Patent
McAlpine et al.

(10) Patent No.: US 12,723,913 B2
(45) Date of Patent: Sep. 1, 2026

(54) PHOTODETECTORS FOR MEASURING REAL-TIME OPTICAL IRRADIANCE

(71) Applicant: Regents of the University of Minnesota, Minneapolis, MN (US)

(72) Inventors: Michael C. McAlpine, Minneapolis, MN (US); David R. Pearson, Maple Grove, MN (US); Xia Ouyang, Shenzhen (CN); Ruitao Su, Allston, MA (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 18/874,948

(22) PCT Filed: Jun. 12, 2023

(86) PCT No.: PCT/US2023/068297

§ 371 (c)(1),
(2) Date: Dec. 13, 2024

(87) PCT Pub. No.: WO2023/244975

PCT Pub. Date: Dec. 21, 2023

(65) Prior Publication Data

US 2025/0369798 A1 Dec. 4, 2025

Related U.S. Application Data

(60) Provisional application No. 63/366,299, filed on Jun. 13, 2022.

(51) Int. Cl.

*G01J 1/42* (2006.01)
*A61B 5/00* (2006.01)

(Continued)

(52) U.S. Cl.

CPC .......... *G01J 1/4204* (2013.01); *A61B 5/0077* (2013.01); *A61B 5/0084* (2013.01);

(Continued)

(58) Field of Classification Search

CPC .. G01J 1/4204; G01J 1/429; G01J 3/42; G01J 3/36; A61B 5/0077; A61B 5/0084;

(Continued)

(56) References Cited

U.S. PATENT DOCUMENTS 10,835,126 B1 * 11/2020 Cong .................. A61B 5/0075
2014/0061486 A1 3/2014 Bao et al.

(Continued)

FOREIGN PATENT DOCUMENTS

GB 2558233 A 2/2017

OTHER PUBLICATIONS

Afzal et al., "Highly efficient self-powered perovskite photodiode with an electron-blocking hole-transport NiOx layer", Scientific Reports, vol. 11, No. 169, Jan. 8, 2021, 14 pp.

(Continued)

*Primary Examiner* — Tony Ko

(74) *Attorney, Agent, or Firm* — Shumaker & Sieffert, P.A.

(57) ABSTRACT

A skin-wearable photodetector module includes an array with a plurality of photodetectors and a plurality of optical filters, and each photodetector is configured to receive an optical input from an optical filter having a central wavelength in a wavelength range of about 100 nm to about 1000 nm. Each photodetector includes a substrate with a first major surface having an electrode thereon, and a second major surface overlying an optical filter, an anode within an interior region of the electrode, an active layer including a.

(Continued)

ternary mixture of an electron donor, an electron acceptor, and at least one charge carrier trap material, and a cathode that contacts the active layer.

20 Claims, 15 Drawing Sheets

(51) Int. Cl.
*B33Y 10/00* (2015.01)
*B33Y 80/00* (2015.01)

(52) U.S. Cl.
CPC ................ *A61B 2560/0214* (2013.01); *A61B 2562/0242* (2013.01); *A61B 2562/12* (2013.01); *B33Y 10/00* (2014.12); *B33Y 80/00* (2014.12)

(58) Field of Classification Search
CPC .... A61B 2560/0214; A61B 2562/0242; A61B 2562/12; A61B 5/0022; A61B 2560/0242; A61B 2562/06; A61B 5/0059; A61B 5/441; A61B 5/6825; B33Y 10/00; B33Y 80/00
See application file for complete search history.

(56) References Cited

U.S. PATENT DOCUMENTS

2016/0218287 A1 7/2016 McAlpine et al.
2019/0305159 A1 10/2019 Santangelo et al.
2020/0368559 A1 11/2020 Poutiatine
2023/0324218 A1* 10/2023 Hegde ...................... G01J 1/32 250/226

OTHER PUBLICATIONS

Armin et al., "Thick junction broadband organic photodiodes", Laser Photonics Review, vo, 8. No. 6, Nov. 2014, p. 924-932.
Azadinia et al., "Improved performance of photoconductive gain hybrid UV detector by trap state engineering of ZnO nanoparticles", Journal of Applied Physics, vol. 122, Oct. 2017, 19 pp.
Badv et al., "An omniphobic lubricant-infused coating produced by chemical vapor deposition of hydrophobic organosilanes attenuates clotting on catheter surfaces", Scientific Reports, vol. 7, No. 1. Dec. 2017, 10 pp.
Bonnassieux et al., "The 2021 flexible and printed electronics roadmap", Flexible and Printed Electronics, vol. 6, May 17, 2021, 48 pp.
Caria et al., "Far UV responsivity of commercial silicon photodetectors", Nuclear Instruments and Methods in Physics Research A, vol. 466, No. 1, Jun. 21, 2001, p. 115-118.
Chow et al., "Organic Photodetectors for Next-Generation Wearable Electronics", Advanced Materials, vol. 32, No. 15, Apr. 16, 2020, 26 pp.
Cui et al., "Single Crystal Microwires of p-DTS(FBTTh2)2 and Their Use in the Fabrication of Field-Effect Transistors and Photodetectors", Advanced Functional Materials, vol. 28, No. 4, Jan. 24, 2018, 8 pp.
Dickey et al., "Eutectic Gallium-Indium (EGaIn): A Liquid Metal Alloy for the Formation of Stable Structures in Microchannels at Room Temperature", Advanced Functional Materials, vol. 18, No. 7, Apr. 11, 2008, pp. 1097-1104.
Dong et al., "An Ultraviolet-to-NIR Broad Spectral Nanocomposite Photodetector with Gain", Advanced Optical Materials, vol. 2, No. 6, Jun. 2014, 549-554 pp.
Gao et al., "Photon-trapping microstructures enable high-speed high-efficiency silicon photodiodes", Nature Photonics, vol. 11, No. 5, Apr. 2017, 9 pp.
Guo et al., "A nanocomposite ultraviolet photodetector based on interfacial trap-controlled charge injection", Nature Technology, vol. 7, Dec. 2012, pp. 798-802.
Gurwitz et al., "Interaction of light with the ZnO surface: Photon induced oxygen "breathing," oxygen vacancies, persistent photoconductivity, and persistent photovoltage", Journal of Applied Physics, vol. 15, Jan. 15, 2014, 10 pp.
Haghiashtiani et al., "3D printed patient-specific aortic root models with internal sensors for minimally invasive applications", Science Advances, vol. 6, Aug. 28, 2020, 11 pp.
Hart et al., "Exposure to Ultraviolet Radiation in the Modulation of Human Diseases", Annual Review of Pathology: Mechanisms of Disease, vol. 14, Jan. 24, 2019, p. 55-81.
Heo et al., "Wireless, battery-free, flexible, miniaturized dosimeters monitor exposure to solar radiation and to light for phototherapy", Science Translational Medicine, vol. 10, Dec. 5, 2018. 13 pp.
Horvath, "Atmospheric Light Absorption—A Review", Atmospheric Environment, vol. 27A, No. 3, Feb. 1993, pp. 293-317.
Hupfeld et al., "Plasmonic Seasoning: Giving Color to Desktop Laser 3D Printed Polymers by Highly Dispersed Nanoparticles", Advanced Optical Materials, vol. 8, No. 15, Aug. 2020, 12 pp.
International Preliminary Report on Patentability from International Application No. PCT/US2023/068297 dated Dec. 26, 2024, 15 pp.
International Search Report and Written Opinion of International Application No. PCT/US2023/068297 dated Dec. 20, 2023, 17 pp.
Jansen Van Vuuren et al., "Organic Photodiodes: The Future of Full Color Detection and Image Sensing", Advanced Materials, vol. 28, No. 24, Jun. 22, 2016, pp. 4766-4802.
Jiang et al., "Printed subthreshold organic transistors operating at high gain and ultralow power", Science, vol. 363, Feb. 15, 2019, pp. 719-723.
Jin et al., "Solution-Processed Ultraviolet Photodetectors Based on Colloidal ZnO Nanoparticles", Nano Letters, vol. 8, No. 6, Jun. 2008, pp. 1649-1653.
Kang et al., "Modular and Reconfigurable Stretchable Electronic Systems", Advanced Materials Technologies, vol. 4, No. 3, Mar. 2019, 6 pp.
Keerthana et al., "Potential risks and benefits of zinc oxide nanoparticles: a systematic review", Critical Reviews in Toxicology, vol. 50, No. 1, Jan. 2020, pp. 47-71.
Kim et al., "Battery-free, stretchable optoelectronic systems for wireless optical characterization of the skin", Science Advances, Aug. 2016, 11 pp.
Kim et al., "Understanding charge trapping/detrapping at the zinc oxide (ZnO)/MAPbI3 perovskite interface in the dark and under illumination using a ZnO/perovskite/ZnO test platform", Nanoscale, vol. 10, Oct. 2018, p. 20377-20383.
Konstantatos et al., "Nanostructured materials for photon detection", Nature Nanotechnology, vol. 5, Jun. 2010. pp. 391-400.
Kublitski et al., "Enhancing sub-bandgap external quantum efficiency by photomultiplication for narrowband organic near-infrared photodetectors", Nature Comunications, vol. 12, No. 4259, Jul. 2021, p. 10 p.
Kwon et al., "An on-skin platform for wireless monitoring of flow rate, cumulative loss and temperature of sweat in real time", Nature Electronics, vol. 4, Apr. 2021, pp. 302-312.
Kwon et al., "Three-dimensional monolithic integration in flexible printed organic transistors", Nature Communications, vol. 10, No. 54, Jan. 3, 2019, 10 pp.
Lee et al., "All 3D-Printed Flexible ZnO UV Photodetector on an Ultraflat Substrate", ACS Sensors, vol. 5, Mar. 2020, pp. 1028-1032.
Li et al., "Ultra-Flexible Visible-Blind Optoelectronics for Wired and Wireless UV Sensing in Harsh Environments", Advanced Materials Technologies, vol. 6, No. 9, Jul. 2021, 11 pp.
Liang et al., "Ferromagnetic CoSe broadband photodetector at room temperature", Nanotechnology, vol. 31, No. 37, Jun. 30, 2020, 9 pp.
Ligon et al., "Polymers for 3D Printing and Customized Additive Manufacturing", Chemical Reviews, Jul. 2017, 79 pp.
Mannsfeld et al., "Highly sensitive flexible pressure sensors with microstructured rubber dielectric lavers", Nature Materials, vol. 9, Oct. 2010, pp. 859-864.

(56) References Cited

OTHER PUBLICATIONS

Matsumoto et al., "Organic Thin-film Solar Cells Using Benzotrithiophene Derivatives Bearing Acceptor Units as Non-Fullerene Acceptors", European Journal of Organic Chemistry, vol. 2021, No. 33, Sep. 7, 2021, p. 4620-4629.
Mccarthy et al., "Poisson's ratio of individual metal nanowires", Nature Communications, Jul. 2014, 7 pp.
Miao et al., "Recent Progress on Photomultiplication Type Organic Photodetectors", Laser and Photonics Reviews, vol. 13, No. 2, Feb. 2019, 38 pp.
Mishra et al., "Soft, wireless periocular wearable electronics for real-time detection of eye vergence in a virtual reality toward mobile eye therapies", Science Advances, vol. 6, Mar. 13, 2020, 12 pp.
Muller et al., "A quick and accurate method to determine the Poisson's ratio and the coefficient of thermal expansion of PDMS", Soft Matter, vol. 15, No. 4, Dec. 2018, pp. 779-784.
Olah et al., "Hydrophobic recovery of UV/ozone treated poly(dimethylsiloxane): adhesion studies by contact mechanics and mechanism of surface modification", Applied Surface Science, vol. 239, No. 3-4, Jan. 2005, p. 410-423.
Park et al., "3D Printed Polymer Photodetectors", Advanced Materials, Aug. 28, 2018, 15 pp.
Ren et al., "Achieving High-Resolution Electrohydrodynamic Printing of Nanowires on Elastomeric Substrates through Surface Modification", ACS Applied Electronic Materials, vol. 3, No. 1, Dec. 29, 2020, 35 pp.
Robinson et al., "Real-Time UV Measurement With a Sun Protection System for Warning Young Adults About Sunburn: Prospective Cohort Study", JMIR Mhealth Uhealth, vol. 9, No. 5, May 2021, 19 pp.
Robinson et al., "Sun exposure reduction by melanoma survivors with wearable sensor providing real-time UV exposure and daily text messages with structured goal setting", Archives of Dermatological Research. vol. 313, No. 8, Oct. 2021, 20 pp.
Schmidt et al., "Sun-Induced Life-Threatening Lupus Nephritis", Annals of New York Academy of Sciences, Jun. 2007, pp. 35-40.
Simone et al., "On the Origin of Dark Current in Organic Photodiodes", Advanced Optical Materials, vol. 8, No. 1, Jan. 3, 2020, 7 pp.
Su et al., "3D printed self-supporting elastomeric structures for multifunctional microfluidics", Science Advances, vol. 6, Oct. 9, 2020, 10 pp.
Su et al., "3D-printed flexible organic light-emitting diode displays", Science Advances, vol. 8, Jan. 7, 2022, 10 pp.
Taylor, "stability of a viscous liquid contained between two rotating cylinders", Philosophical Transactions of the Royal Society A, Feb. 1923, pp. 541-542.
Vaynzof et al., "Direct Observation of Photoinduced Bound Charge-Pair States at an Organic-Inorganic Semiconductor Interface", Physical Review Letters, vol. 108, Jun. 15, 2012, 5 pp.
Voroshazi et al., "Long-term operational lifetime and degradation analysis of P3HT: PCBM photovoltaic cells", Solar Energy Materials & Solar Cells, vol. 95, No. 5, May 2011, p. 1303-1307.
Vudayagiri et al., "Factors affecting the surface and release properties of thin polydimethylsiloxane films", vol. 45, Jan. 23, 2013, p. 871-878.
Wang et al., "Crosslinking Effect on Polydimethylsiloxane Elastic Modulus Measured by Custom-Built Compression Instrument", Journal of Applied Polymer Science, vol. 131, No. 22, Nov. 15, 2014, 4 pp.
Xie et al., "Flexible Photodetectors Based on Novel Functional Materials", Small, vol. 13, No. 43, Nov. 20, 2017, 36 pp.
Xie et al., "Heat Resisting Metallic Meta-Skin for Simultaneous Microwave Broadband Scattering and Infrared Invisibility Based on Catenary Optical Field", Advanced Materials Technologies, vol. 4, No. 2, Feb. 2019, 7 pp.
Zhang et al., "3D μ-printing of polytetrafluoroethylene microstructures: a route to superhydrophobic surfaces and devices", Applied Materials Today, vol. 19, Jun. 2020, 30 pp.
Zhang et al., "Flexible Narrowband Ultraviolet Photodetectors with Photomultiplication Based on Wide Band Gap Conjugated Polymer and Inorganic Nanoparticles", ACS Applied Materials and Interfaces, vol. 10, No. 28, Jul. 18, 2018, p. 24064-24074.
Zhao et al., "Photomultiplication type organic photodetectors based on electron tunneling injection", Nanoscale, vol. 12, No. 2, Dec. 2019, p. 1091-1099.
Zhou et al., "Significant Detectivity Enhancement of Broad Spectral Organic-Inorganic Hybrid Photodiodes by C60 Film as Hole-Blocking Layer", Nanoscale Research Letters, vol. 17, No. 1, Jan. 2022, 9 pp.
Zhou et al., "Ultrahigh Gain Polymer Photodetectors with Spectral Response from UV to Near-Infrared Using ZnO Nanoparticles as Anode Interfacial Layer", Advanced Functional Materials, vol. 26, No. 36, Sep. 26, 2016, p. 6619-6626.
Zhu et al., "3D printed deformable sensors", Science Advances, vol. 6, Jun. 17, 2020, 10 pp.
Zhu et al., "3D-printed multifunctional materials enabled by artificial-intelligence-assisted fabrication technologies", Nature Reviews, vol. 6, Jan. 2021, pp. 27-47.
Zhu et al., "Exciton Binding Energies in Organic Photovoltaic Materials: A Theoretical Perspective", The Journal of Physical Chemistry C, vol. 126, No. 1, Dec. 29, 2021, pp. 14-21.
Zou et al., "Recent Advances and a Roadmap to Wearable UV Sensor Technologies", Advanced Materials Technologies, vol. 5, No. 4, Apr. 2020, 31 pp.

* cited by examiner

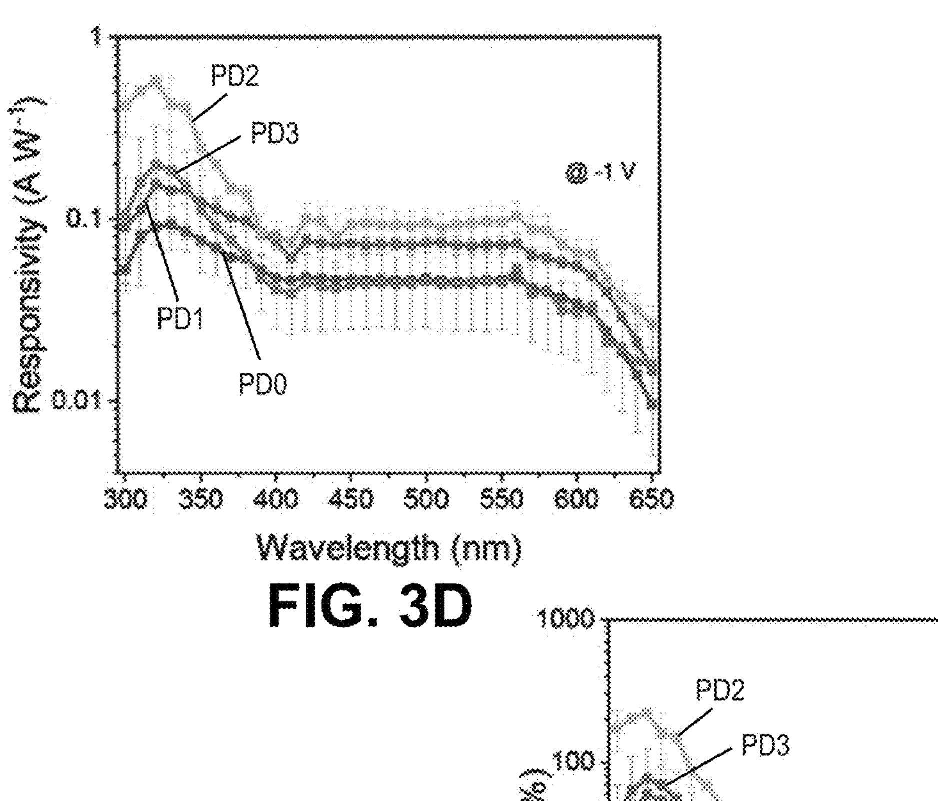
FIG. 3D
FIG. 3E
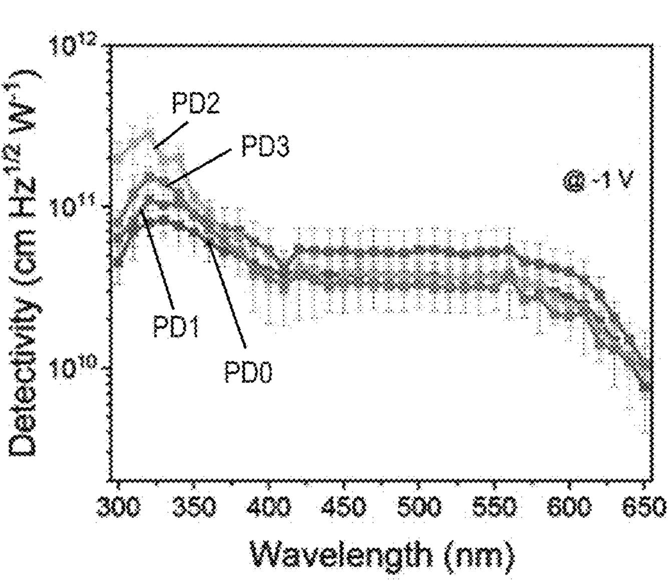
FIG. 3F

PHOTODETECTORS FOR MEASURING REAL-TIME OPTICAL IRRADIANCE

This application is a National Stage application under 35 U.S.C. § 371 of PCT Application No. PCT/US2023/068297, filed on Jun. 12, 2023, claiming priority to and the benefit of U.S. Provisional Patent Application No. 63/366,299, filed Jun. 13, 2022, the entire contents of each of which is incorporated herein by reference.

GOVERNMENT RIGHTS

This invention was made with government support under EB020537 awarded by the National Institutes of Health. The government has certain rights in the invention.

This invention was made with government support under ECCS-2025124 awarded by the National Science Foundation. The government has certain rights in the invention.

BACKGROUND

Photodetectors can be applied to a surface to measure real-time optical irradiance incident on the surface. For example, wearable and skin-interfaced electronic devices that continuously monitor environmental signals in-situ and serve as real-time health-profiling strategies have potential for mitigating the severity of environmentally-sensitive diseases. For example, some skin diseases, such as lupus erythematosus (LE), an autoimmune disorder with characteristic skin and systemic manifestations, may be triggered or exacerbated via UV or visible exposure from the sun or even ambient indoor light. Broad-spectrum environmental light exposure, particularly in the UVB band covering the spectral range of 280 to 310 nm and the UVA band spanning the spectral range of 310 to 400 nm, exerts a variety of clinical repercussions in LE patients.

Accordingly, there is a need for a skin-interfaced photodetector system that quantitatively measures irradiance across clinically relevant spectral bands, which can make possible the assessment of disease-exacerbating light exposures in-situ.

SUMMARY

In general, the present disclosure is directed to photodetectors that can be interfaced with a planar or a non-planar surface to measure real-time optical irradiance on the surface. In one example, the photodetectors form a component of a skin-wearable photodetector module that can be removably attached to the skin of a patient to monitor light exposure to an area of the skin. The data obtained from the photodetector can be used to, for example, profile, guide treatment of, or provide prevention or risk mitigation strategies for photosensitive or photoresponsive skin diseases.

The photodetectors of the present disclosure have ultraviolet (UV)-enhanced broadband response, and can be made with polymeric materials that are both stretchable and flexible. In one example, when directly applied to a non-planar or moveable surfaces such as skin, the photodetectors can provide more precise and consistent irradiance measurements across a selected spectral band important to dermatological health. To provide enhanced response in the UV range, the photodetectors include a hybrid active material system including organic polymeric photoactive materials doped with a charge carrier trap material such as, for example, UV-absorbing inorganic nanoparticles, quantum dots, organic dyes, and the like.

In some examples, a plurality of photodetectors may be arranged in an array to form a photodetector module. Each photodetector in the array receives an optical input from an optical filter having a central wavelength in a selected wavelength range. Each photodetector in the array provides an output signal that allows a clinician to monitor patient skin exposure to light in the wavelength range transmitted by the optical filter associated with the photodetector.

In some examples, the photodetector module including the array of photodetectors is a component of a photodetection system. The photodetector module provides output signals to a portable console that can be used to continuously monitor broadband irradiance in-situ. In some examples, the stand-alone skin-interfaced patient photodetection system can be used to detect natural irradiance to a selected area of the skin of a patient within the wavelength range of 100 nm to 1000 nm for a predetermined period time.

In some examples, the photodetectors can be quickly and inexpensively made using a three-dimensional (3D) printing process such as extrusion printing. In one application, a medical practitioner can use the 3D printing process to rapidly make a custom photodetector, which may then be associated with an optical filter providing optical input signals over a predetermined wavelength range. A plurality of photodetectors may be arranged in an array to form a photodetector module configured to monitor skin light exposure in a selected wavelength range, which can make possible profiling and/or treatment of a disease caused or exacerbated by UV light exposure.

In one aspect, the present disclosure is directed to a skin-wearable photodetector module, including: an array including a plurality of photodetectors, wherein each photodetector in the array of photodetectors receives an optical input from an optical filter having a central wavelength in a wavelength range of about 100 nm to about 1000 nm, and wherein each photodetector includes: a substrate having a first major surface with an electrode thereon, and a second major surface overlying an optical filter in the array of optical filters; an anode within an interior region of the electrode; an active layer including a ternary mixture of an electron donor, an electron acceptor, and at least one charge carrier trap material; and a cathode that contacts the active layer.

In another aspect, the present disclosure is directed to a photodetection system configured for removable attachment to human skin. The system includes: a skin-wearable photodetector module, including: an array with a plurality of photodetectors, wherein each photodetector in the array receives an optical input from an optical filter having a central wavelength selected in a wavelength range of about 100 nm to about 1000 nm, and wherein each photodetector includes: a substrate with a first major surface and a second major surface, wherein the substrate includes a polymeric material that is transparent to incident light with a wavelength of about 100 nm to about 1000 nm, and wherein the second major surface of the substrate is adjacent to an optical filter in the array of optical filters; a metal electrode on the first major surface of the substrate, wherein the metal electrode includes an interior region; an anode on the first major surface of the substrate and overlying the interior region of the metal electrode, wherein the anode includes a conducting or semiconducting polymer; a metal cathode; and an active layer between the metal anode and the metal cathode, wherein the active layer includes a ternary mixture of a polymeric electron donor, a polymeric electron acceptor, and inorganic UV absorbing particles, and wherein the active layer has a ratio by weight, based on a total weight of the active layer, of: about 1.0 parts of polymeric electron donor:about 0.5 parts to about 1.2 parts of a polymeric primary electron acceptor:greater than about 0 parts and up to about 5 parts of UV absorbing inorganic particles; and wherein the photodetectors and the optical filters are within an encapsulating layer of a polymer, and wherein the encapsulating layer further includes a connector circuit connected to the metal electrode; a connector connected to the connector circuit in the encapsulating layer; and a control console connected to the connection circuit, wherein the control console includes a signal processing module, a data processing module, and a power supply.

In another aspect, the present disclosure is directed to a method of making a photodetector with a three-dimensional (3D) extrusion process, the method including: extruding a first conductive ink on a first major surface of a substrate to form an electrode, wherein the substrate includes a polymeric material that is transparent to incident light with a wavelength of about 100 nm to about 1000 nm; extruding a conducting or semiconducting polymer onto the first major surface of the substrate and within an interior region of the electrode to form an anode; extruding a ternary mixture of a polymeric electron donor, a polymeric electron acceptor, and a charge carrier trap material onto the anode to form an active layer; and extruding a second conductive ink onto the active layer to form a cathode.

In another aspect, the present disclosure is directed to a method for real-time monitoring of optical irradiance in situ on skin of a patient, the method including applying to the skin of the patient a skin-wearable photodetector module, the photodetector module including an array with a plurality of photodetectors, wherein each photodetector in the array of photodetectors receives an optical input from an optical filter having a central wavelength selected in a wavelength range of about 100 nm to about 1000 nm, and wherein each photodetector in the array of photodetectors includes: an active layer between the metal anode and the metal cathode, wherein the active layer includes a ternary mixture of a polymeric electron donor, a polymeric electron acceptor, and a charge carrier trap material; and monitoring, with the photodetector module, irradiance on the skin of the patient to diagnose or treat a medical condition.

In another aspect, the present disclosure is directed to a method for making a monitoring optical irradiance on a selected region of the skin of a patient, the method including: selecting a plurality of optical filters for monitoring the irradiance over a desired wavelength range, wherein each optical filter has a central wavelength in a wavelength rage of about 100 nm to about 1000 nm; forming, with a three-dimensional (3D) extrusion process, a photodetector over each of the optical bandpass filters, wherein the 3D extrusion process includes extruding for each photodetector a ternary mixture of a polymeric electron donor, a polymeric electron acceptor, and inorganic UV-absorbing nanoparticles onto the anode to form an active layer.

In another aspect, the present disclosure is directed to a photodetector including an active layer having a ternary mixture of a polymeric electron donor, a polymeric electron acceptor, and UV absorbing particles, wherein the active layer includes a ratio by weight, based on a total weight of the active layer, of: about 1.0 parts of polymeric electron donor:about 0.5 parts to about 1.2 parts of a polymeric primary electron acceptor:greater than about 0 parts and up to about 3 parts of inorganic particles.

In another aspect, the present disclosure is directed to a method for real-time monitoring of optical irradiance on a surface, the method including applying to the surface a skin-wearable photodetector module, the photodetector module including an array having a plurality of photodetectors, wherein each photodetector in the array of photodetectors receives an optical input from an optical filter having a central wavelength selected in a wavelength range of about 100 nm to about 1000 nm, and wherein each photodetector in the array of photodetectors includes: an active layer between the metal anode and the metal cathode, wherein the active layer includes a ternary mixture of a polymeric electron donor, a polymeric electron acceptor, and a charge carrier trap material; and monitoring, with the photodetector module, irradiance on the skin of the patient to diagnose or treat a medical condition.

In another aspect, the present disclosure is directed to a photodetector module, including: an array having a plurality of photodetectors, wherein each photodetector in the array of photodetectors receives an optical input from an optical filter having a central wavelength in a wavelength range of about 100 nm to about 1000 nm, and wherein each photodetector includes: a substrate with a first major surface with an electrode thereon, and a second major surface overlying an optical filter in the array of optical filters; an anode within an interior region of the electrode; an active layer including a ternary mixture of an electron donor, an electron acceptor, and at least one charge carrier trap material; and a cathode that contacts the active layer; wherein the photodetector module is implanted in a human body.

The details of one or more examples are set forth in the accompanying drawings and the description below. Other features, objects, and advantages will be apparent from the description and drawings, and from the claims.

BRIEF DESCRIPTION OF DRAWINGS

FIG. 1B-1 is a schematic illustration of a 3D printed photodetector module of FIG. 1A.

FIG. 1B-2 is a diagram showing the central wavelengths of the optical filters in the array of photodetectors in the photodetector module of FIG. 1B-1.

FIG. 1B-3 is an exploded view of one photodetector in the photodetector module of FIG. 1B-1 associated with an optical filter.

FIGS. 3D-F are plots showing responsivity (FIG. 3D), EQE (FIG. 3E), and detectivity (FIG. 3F), respectively, at a bias voltage of −1 V of the photodetectors printed with the various active materials of FIG. 2A (n=3). Data are presented as mean±SD.

Like symbols in the drawings indicate like elements.

DETAILED DESCRIPTION

Figure 1A:
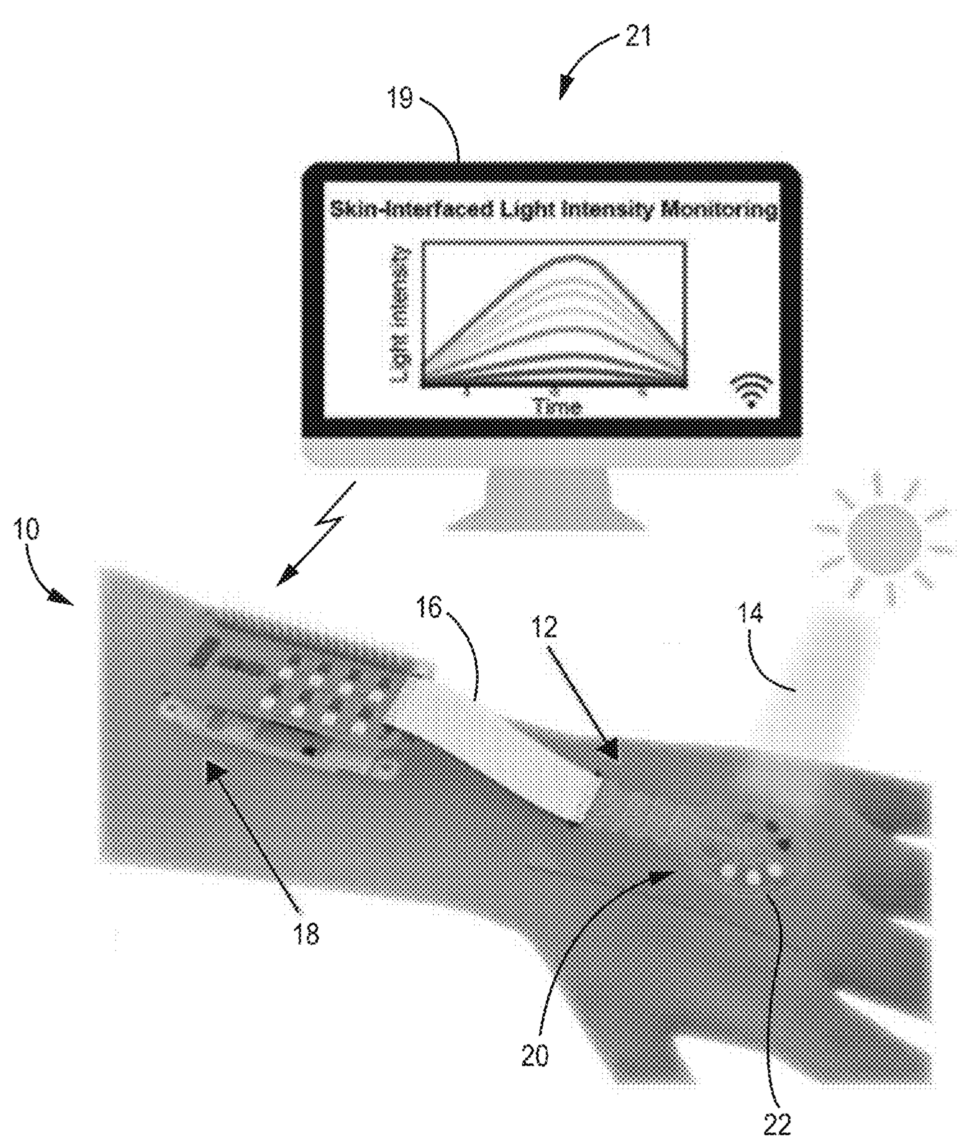
FIG. 1A is a schematic illustration of an embodiment of a skin-wearable photodetection system of the present disclosure, which includes a photodetector module, a flexible connector, and a control console for signal processing and wireless data transmission.

To monitor the light incident on a non-planar or flexible surface such as, for example, human skin, silicon photodetectors, which are compatible with silicon electronics and have a low-noise signal profile, can have limited mechanical flexibility and weak absorption over a broadband spectrum. In some examples, the photodetectors of the present disclosure are both flexible and stretchable. The photodetectors can utilize organic semiconductors as photoactive materials, which have good mechanical flexibility, and are useful for attachment on a non-planar and movable surface such as the skin of a patient. Moreover, compared to silicon-based materials, the photodetectors described herein can be made quickly with solution-based processing methods such as 3D printing, have tunable optoelectronic performance, more uniform affinity to the target surface, and lower cost.

However organic photoactive materials can have lower sensitivity compared to inorganic photodiodes. Inorganic photoactive materials generally have higher sensitivities due to the avalanche effect or impact ionization, while photodetectors with organic photoactive materials can have a limited capacity to detect weak light signals. In some examples, this reduced capacity to detect weak light signals can be a result of reduced charge generation yields caused by the larger exciton binding energies and disordered molecular stacking of organic semiconductor materials. This limited capability can diminish the application of photodetectors with organic active materials, since incident UV light can be less intense than visible light due to, for example, absorption by ozone, water vapor, and other molecules in the air.

For a wearable photodetector device to efficiently function in a low-power and electrically safe state, the hybrid active materials should be formulated to achieve a high external quantum efficiency (EQE) under low bias voltage. EQE represents a ratio of incident photons to converted electrons (e.g., current), such that a higher EQE may result in less power consumption for a desired output. For example, for a more power sensitive device, the hybrid active material may have a relatively high EQE (e.g., greater than 100%), while for a less power sensitive device, the hybrid active material may have a relatively lower EQE (e.g., greater than about 10%). Therefore, to enhance the photoresponse, the organic active materials in the photodetectors of the present disclosure introduce trap states for charge tunneling injection, which can amplify the photocurrent using the photomultiplication (PM) effect. With this approach, multiple charge carriers can be gathered when one incident photon is absorbed, resulting in EQEs that can exceed 100%, or 200%, or 1000%, or even greater than 10,000%.

To provide this enhanced capability to detect UV light, the photodetectors of the present disclosure utilize an active layer with a charge carrier trap material such as, for example, UV-absorbing inorganic nanoparticles, quantum dots, organic dyes, and mixtures and combinations thereof. In the present application, the term charge carrier trap material refers to materials with trap states for charge carriers such as, for example, holes and electrons. Charge trap carrier compounds are discussed in, for example, Haneef et al., *Charge Carrier Traps in Organic Semiconductors: A Review of the Underlying Physics and Impact on Electronic Devices*, J. Mater. Chem. C, 2020, 8, 759-787; and Miao et al., *Recent Progress on Photomultiplication Type Organic Photodetectors*, Laser & Photonic Reviews, 12 Dec. 2018.

In one example, the charge carrier trap material includes one or more UV-absorbing inorganic nanoparticles such as, for example, zinc oxide (ZnO), titanium dioxide ($TiO_2$), cerium oxide ($CeO_2$) or the like as a carrier trap material. In the present application, the term nanoparticle refers to particles having a largest measurable dimension of about 1 nm to about 100 nm. The inorganic nanoparticles can trap electrons due to local defects on their surfaces, and inorganic particles such as ZnO, $TiO_2$, and $CeO_2$ nanoparticles (NPs), which are widely-used low-cost metal-oxides in commercial sunscreens, can be deployed in UV photodetectors due to their wide direct bandgap. In the photodetectors of the present disclosure, the organic semiconductor material can be doped with the inorganic nanoparticles to provide a hybrid active material with enhanced photoresponse in the UV range. In some examples, the photodetectors of the present disclosure demonstrated a responsivity of 0.51 A $W^{-1}$ and an EQE of >100% at 310 nm at a bias of as low as −1 V, which was found to be suitable for battery-operated wearable devices.

Three-dimensional (3D) printing technologies can fabricate devices from a broad palette of materials, without requiring conventional fabrication techniques such as spin-coating, templates, photolithography, or high vacuum metal deposition. Among currently available 3D printing technologies such as inkjet printing, aerosol jet printing, optical printing, and powder bed fusion-based printing, extrusion-based 3D printing can accommodate a broad range of printable viscosities of multi-functional inks. Furthermore, extrusion-based 3D printing is suitable for fully 3D printed functional devices using a 'multi-scale' printing approach, incorporating nanoscale inks printed at the micron scale to fabricate macro-scale devices, and the integration of multiple functionalities on rigid or flexible substrates, or even on moving objects.

A flexible, stretchable, and substrate can provide a photodetector that conforms to a non-planar surface such as the human body naturally and safely. In some examples, the photodetectors and photodetector modules of the present disclosure utilize biocompatible substrate and encapsulant materials such as polydimethylsiloxane (PDMS). In some examples, the surfaces of the PDMS substrate materials can be modified to provide more uniform wetting of the materials to be applied thereon. In some examples, surface modification methods such as UV-ozone (UVO) treatment, plasma treatment, or other chemical coatings can be used to regulate the wettability of the PDMS substrate, which helps to precisely define the pattern and layout of the electrodes and active components of the device. The flexible and functional devices may then be 3D printed on the PDMS substrate and transferred to human skin for monitoring of health-related environmental signals.

In one example, the flexible photodetectors of the present disclosure, printed on PDMS films, demonstrated reliable performance stability during both optical and mechanical tests, and can be used to continuously detect and monitor light intensity under natural sunlight over an extended time period.

Figures 1, 1B, 2, 3:
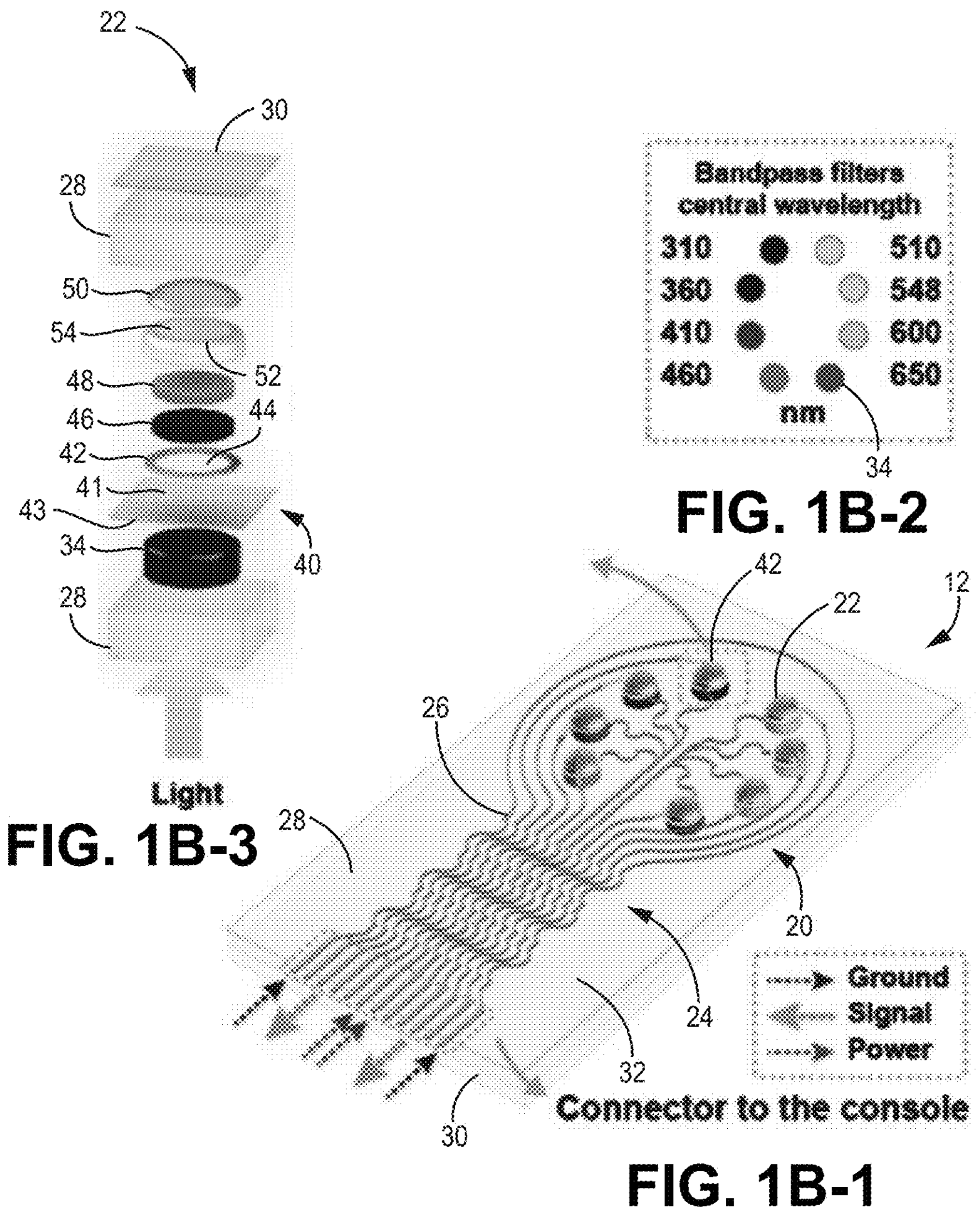

Referring now to FIG. 1A, a skin-interfaced photodetector system 10 includes a skin-wearable photodetector module 12 with an array 20 including a plurality of photodetectors 22 (shown in more detail in FIG. 1B). Each photodetector 22 in the array 20 is associated with an optical filter, which may also optionally be 3D printed, configured to provide an optical input signal to the photodetector over a predetermined wavelength range of ambient light 14. The photodetector module 12 includes connector circuitry electrically connected to a flexible connector 16 such as, for example, a flat flexible cable (FFC). The flexible connector 16 is in turn electrically connected to a control console 18 that includes a signal processor module, a data processing module, and a power supply (shown in more detail in FIG. 1C). In some examples, the control console 18 may be directly or wireless interfaced with a display device 19 to present data to a user such as, for example, a physician or a medical clinician. In some examples, the display device 19 can be part of an external programmer 21 that can be used by the user to provide instructions to the photodetector module 12.

In some examples, the programmer 21 may include a display screen (e.g., a liquid crystal display (LCD) or a light emitting diode (LED) display) that presents information to a user. In addition, in some examples the control console 18 or the programmer 21, or both, can include a touch screen, keypad, buttons, a peripheral pointing device, voice activation, or another input mechanism that allows the user to navigate through the user interface of the control console 18 and provide input. If the control console 18 or the programmer 21 include buttons and a keypad, the buttons may be dedicated to performing a certain function, e.g., a power button, the buttons and the keypad may be soft keys that change in function depending upon the section of the user interface currently viewed by the user, or any combination thereof. In other examples, the programmer 21 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure device.

When the control console 18 is configured for use by a clinician, the programmer 21 may be used to transmit instructions to the control console 18, and to receive measurements and other data from the photodetector module 12. Example instructions may include requests to set parameters for controlling the photodetectors 22 in the array 20 of the photodetector module 12. The clinician may also configure and store operational parameters for the photodetector module 12 with the aid of the programmer 21. In some examples, programmer 21 assists the clinician in the configuration of the photodetector module 12 by providing a system for identifying potentially beneficial operational parameter values.

Whether programmer 21 is configured for clinician or patient use, programmer 21 is configured to communicate with the control console 18 and, optionally, another computing device (not illustrated in FIG. 1A), via wireless communication. The programmer 21, for example, may communicate via near-field communication technologies (e.g., inductive coupling, NFC or other communication technologies operable at ranges less than 10-20 cm) and far-field communication technologies (e.g., RF telemetry according to the 802.11 or specification sets available under the trade designation Bluetooth, or other communication technologies operable at ranges greater than near-field communication technologies).

The console 18 further supplies a selected bias, for example, about −1 V, to the photodetectors 22 in the photodetector array 20 to yield photocurrent signals. The photocurrent signals may be stored and plotted by the console, the programmer, or other computing device. With an embedded Wi-Fi module in the console, information regarding light intensity data and charts can be wirelessly transmitted to the programmer 21 or other computing device, and be made accessible via a web browser for real-time monitoring of light exposure to the skin of a patient.

The photodetector module 12 is shown in more detail in FIG. 1B-1. In the example shown in FIG. 1B-1, the photodetector module includes an array 20 of photodetectors 22. In the example of FIGS. 1A and 1B-1, the array 20 includes 8 photodetectors 22, but any number of photodetectors 22 may be used for a particular application of the photodetector module 12. Each of the photodetectors 22 in the array 20 includes a different optical filter that provides an optical input signal to the photodetector 22 in a specific wavelength range. In various examples, the optical filters can include any device, membrane, or coating that selectively transmits light of a particular wavelength.

In the example of FIG. 1B-1, eight different optical filters 34, with central wavelengths ranging from 310 nm to 650 nm (FIG. 1B-2), were placed on the device side that received the incident light 14. In the example of FIG. 1B-2, each optical filter 34 had a central wavelength differing by about ±50 nm from a neighboring optical filter in the array 20 to provide overall coverage of a UV-visible wavelength range of 310 nm to 650 nm, but of course any combination of optical filters 22 can be used to be used to monitor irradiance on a surface in any predetermined wavelength range from about 100 nm to about 1000 nm.

In the example shown in FIGS. 1A and 1B-1, the photodetectors 22 in the array 20 are circumferentially arranged about a central point, but any suitable arrangement of photodetectors 22 may be used in the array 20. The photodetectors 22 are each connected via a connection circuit 24, which includes an arrangement of wires 26. The connection circuit 24 may be readily connected and disconnected to the connector 16 (FIG. 1A) via any suitable connector such as, for example, a male-female plug-in connector (not shown in FIG. 1B-1).

In the design of the example of the connection circuit shown in FIG. 1B-1, which is not intended to be limiting, each photodetector 22 is connected to one individual signal line, and four photodetectors shared one common power line as a group. A protective grounding line enclosed the photodetector array to reduce the external electromagnetic interference to the device. Thus, twelve pins were used in total as connectors to the console. The serpentine shape of the electrodes 26 was chosen in accordance with the design rules in stretchable electronics, which aid in enduring the increased tensile strain that occurs from movement-induced deformation of the wearable device 10.

The array 20 of the photodetectors 22, as well as the connection circuit 24, are encapsulated in a flexible and stretchable encapsulating layer 28 of a polymer. Any suitable polymer may be used to form the encapsulating layer 28, and silicones such as polydimethylsiloxane (PDMS) have been found to provide suitable levels of flexibility, stretchability, and biocompatibility with human skin.

In some examples, an optional adhesive layer 30 may be applied on all or a portion of an exterior surface 32 of the encapsulating layer 28 to provide enhanced adhesion to the skin of a patient.

A schematic exploded view of a photodetector 22 in the array 20 is shown in FIG. 1B-3. As shown in FIG. 1B-3, light 14 incident on the photodetector 22 successively passes through the transparent encapsulation layer 28, and enters an optical filter 34 with a central wavelength in a predetermined wavelength range. An optical input signal having the wavelength range selected by the optical filter 34 then encounters a substrate 40 with a first major surface 41 and a second major surface 43 overlying the optical filter 34. The substrate 40 may be chosen from any stretchable and flexible polymeric material that is transparent to the optical signal transmitted by the optical filter. In some examples, the substrate 40 can be transparent to optical signals having a wavelength of about 100 nm to about 1000 nm, or about 100 nm to about 400 nm, or about 400 nm to about 700 nm. In some examples, the substrate 40 is a silicone material such as, for example, PDMS An electrode 42 resides on the first major surface 41 of the substrate 40. The electrode 42 includes an interior region 44. The electrode 42 may be formed from any conductive material, and metals such as Au, Ag, Cu, mixtures thereof and alloys thereof, have been found to be particularly suitable. As shown schematically in FIG. 1B-1, the electrodes 42 of each photodetector 22 are electrically connected to the electrodes 26 of the connection circuit 24. The electrode 42 shown in FIG. 1B-3 has an annular shape, but electrodes of any shape having an open interior region may be used.

In some examples, as discussed in more detail below, the first major surface 41 of the substrate 40 may optionally be surface modified to alter the wettability of the surface with respect to the metal-containing material of the electrode 42.

The optical input signal filtered through the optical bandpass filter 34 then propagates through a transparent anode layer 46. The anode layer 46 can be formed from any conducting or semiconducting material, and in some examples the anode layer is formed from organic materials such as the intrinsically conducting polymer mixture of poly(3,4-ethylenedioxythiophene):polystyrene sulfonate (PEDOT:PSS).

The organic conducting material of the transparent anode layer 46 excites a layer of an active material 48 that includes an electron donor material, an electron acceptor material, and a charge carrier trap material. In some examples, the active layer is a hybrid of organic materials and an inorganic charge carrier trap material such as one or more UV-absorbing inorganic nanoparticles. Suitable UV-absorbing inorganic nanoparticles include, for example, ZnO, $TiO_2$, $CeO_2$, and mixtures and combinations thereof. In another example, the charge carrier trap material may be an organic material that absorbs UV light such quantum dots, organic dyes, and the like.

Referring again to FIG. 1B-3, in some examples, which are not intended to be limiting, the electron donor material in the active layer 48 is an organic polymeric electron donor compound such as a polythiophene, and the organic electron acceptor material includes a functionalized fullerene compound. In one example, the material making up the active layer 48 includes a ternary mixture of poly(3-hexylthiophene) (P3HT), [6,6]phenyl C61-butyric acid methyl ester (PCBM), which have bandgaps of ca. 1.9 eV and ca. 2.2 eV, respectively, and the charge carrier trap material. For example, the charge carrier trap material can include at least one UV-absorbing inorganic nanoparticle such as ZnO, $TiO_2$, $CeO_2$, and the like, (bandgap=ca. 3.4 eV), which increase the light sensitivity in the UV range.

In some examples, the inorganic nanoparticles in the active layer include ZnO, and in some examples, the inorganic nanoparticles consist essentially of ZnO. In the present application, consisting essentially of ZnO means that the UV absorbing inorganic particles in the active layer include ZnO and less than 1 wt % of incidental impurities. The inorganic UV absorbing active materials absorb incoming photons and produce excitons that diffuse in the hybrid materials and disintegrate as free charge carriers, including holes and electrons, at the polymer/polymer and polymer/nanoparticle interfaces.

In some examples, the ratio by weight of the composition of the active layer 48, based on the total weight of the active layer, is about 1 part polymeric electron donor:about 0.5 parts to about 1.2 parts of the polymeric electron acceptor: greater than about 0 and up to about 5 parts inorganic particles. In some examples, the composition of the active layer 48 was about 1 part P3HT:about 0.8 parts PCBM:about greater than about 0 parts and up to about 3 parts inorganic particles. In the above examples, the ratios of the composition of the active layer can vary by approximately ±10%, or ±5%.

In some examples, the composition of the active layer 48 was about 1 part P3HT:about 0.8 parts PCBM:about 0.5 parts to about 2.5 parts inorganic particles. In some examples, the composition of the active layer 48 was about 1 part P3HT:about 0.8 parts PCBM:about 0.5 parts to about 2.5 parts inorganic particles, or about 1 part P3HT:about 0.8 parts PCBM:greater than about 0 parts and up to about 2.0 parts inorganic particles.

In some examples, when the inorganic particles consisted essentially of ZnO, the composition of the active layer was about 1 part P3HT:about 0.8 parts PCBM:about 1 part ZnO, about 1 part P3HT:about 0.8 parts PCBM:about 2 parts ZnO, or about 1 part P3HT:about 0.8 parts PCBM:about 3 parts ZnO.

Charge carriers are collected by the anode 46 and a cathode 50. In some examples, the cathode 50 can be made from conductive metals such as Ag, Au, Cu, eutectic gallium indium (EGaIn), and mixtures and alloys thereof. In some examples, the cathode 50 can be formed from EGaIn alloyed with Cu, or EGaIn mixed with a polymeric modifier such as a silicone.

The collected charge carriers generate a photocurrent signal. Some electrons are trapped by the charge carrier trap material of the active layer 48 instead of being collected by the cathode 50, which enhances the charge tunneling injection and triggers a photomultiplier (PM) effect, which amplifies the photocurrent signal and improves the photoresponse of the photodetector 22.

Referring again to FIG. 1B-3, in some examples the photodetector 22 includes an optional insulating layer 52. In some examples, which are not intended to be limiting, the insulating layer 52 can be formed from a polymeric material such as a silicone. In the example of FIG. 1B-3, the insulating layer 52 has a generally cylindrical shape that encircles both the anode 46 and the active layer 48. The cylindrical insulating layer 52 has an open interior region 54, which houses the cathode 50. The insulating layer 52 thus maintains the separation of the anode 46 and the cathode 50, and can reduce the likelihood of short circuits within the photodetector 22 as the photodetector module 12 is flexed and stretched on the skin of a patient.

Figure 1C:
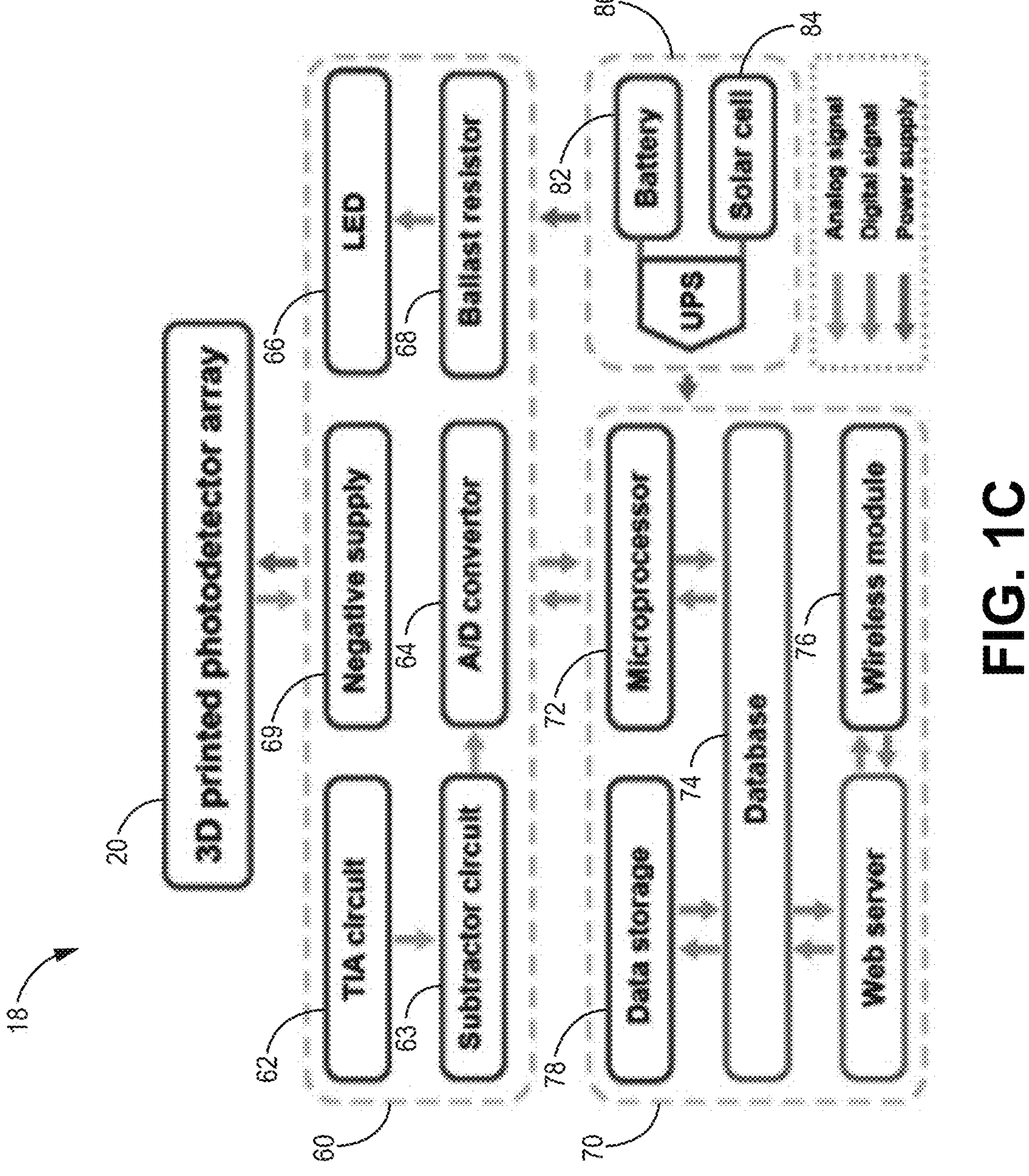
FIG. 1C is a schematic block diagram of the control console in the photodetection system of FIG. 1A.

Referring now to the generalized schematic in FIG. 1C, the control console 18 of the light intensity monitoring system 10 includes a signal processing module 60, a data processing module 70, and a power supply 80. In the example of FIGS. 1A-C, the FFC 16 connects the photodetector array 20 to the signal processing module 60. The photocurrent signals generated by the photodetectors 22 in the array 20 are processed by a transimpedance amplifier (TIA) circuit 62, which converts the current signals to voltage signals. The voltage signals generated by the TIA circuit 62 are then processed by subtractor circuits 63 and further amplified to improve dynamic range, and the amplified analog signals are converted by an analog/digital converter (ADC) 64 to digital signals. In some examples, the signal processing module 60 further includes a feedback signal that triggers a light-emitting diode (LED) 66 via a ballast resistor 68 on the signal processing board to indicate the status of the console when the photocurrent signals are being processed. The signal processing module 60 further includes a negative bias voltage supply module 69, which maintains a bias voltage across the photodetectors 22 in the array 20.

The signals from the signal processing module were further processed by a processor 72 in the data processing module 70. In various examples, the processor 72 may include any one or more of a microprocessor, a controller, a digital signal processor (DSP), an application specific integrated circuit (ASIC), a field-programmable gate array (FPGA), or equivalent discrete or analog logic circuitry. In some examples, the processor 72 may include multiple components, such as any combination of one or more microprocessors, one or more controllers, one or more DSPs, one or more ASICs, or one or more FPGAs, as well as other discrete or integrated logic circuitry. The functions attributed to the processor 72 herein may be embodied as software, firmware, hardware, or any combination thereof.

The digital signals can be stored or buffered locally in a memory database 74 that can be exported by the processor 72 as readable files or viewed on a graphically interactive webpage via a wireless connection via a wireless module 76. In some examples, the database 74 may export the data to an external data storage site (not shown in FIG. 1C) via a data storage module 78. The database 74 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital or analog media.

The power supply module 80 is configured to be uninterruptable, which in this application means that the power supply 80 continuously supplies electric power to the photodetectors 22 in the array 20 over a predetermined period of time such as, for example 8 hours, 16 hours, 24 hours, 48 hours, and the like. The power supply module 80 can include a battery, or in some examples the power supply module 80 manages the power sources among a battery 82, a solar cell 84, and a direct current power source, so that a stable power source could be continuously provided to the photodetector array 20 for extended periods of real-time monitoring of light intensity.

In another aspect, the present disclosure relates to a method for making a photodetector using a 3D printing process. Any 3D printing technique may be used, and suitable examples include inkjet printing, aerosol jet printing, optical printing, powder bed fusion-based printing, extrusion-based printing, and combinations thereof. In some examples, extrusion-based 3D printing can accommodate a broad range of printable viscosities of multi-functional inks that can be used to form one or more functional layers of the photodetector including, but not limited to, the electrode, the anode, the cathode, and the active layer, as well as non-functional layers like insulating layers, substrates, adhesive layers, and the like. In some examples, the components of the photodetector module such as, for example, the optical filters and the encapsulating layer, may also be formed using an extrusion-based 3D printing process. For example, suitable optical filters can be formed by polymeric layers, or polymeric layers including particles, organic dyes, dielectric materials, and the like. Furthermore, extrusion-based 3D printing is suitable for fully 3D printed functional devices using a 'multi-scale' printing approach, incorporating nanoscale inks printed at the micron scale to fabricate macro-scale devices, and the integration of multiple functionalities on rigid or flexible substrates, or even on moving objects.

Figure 8:
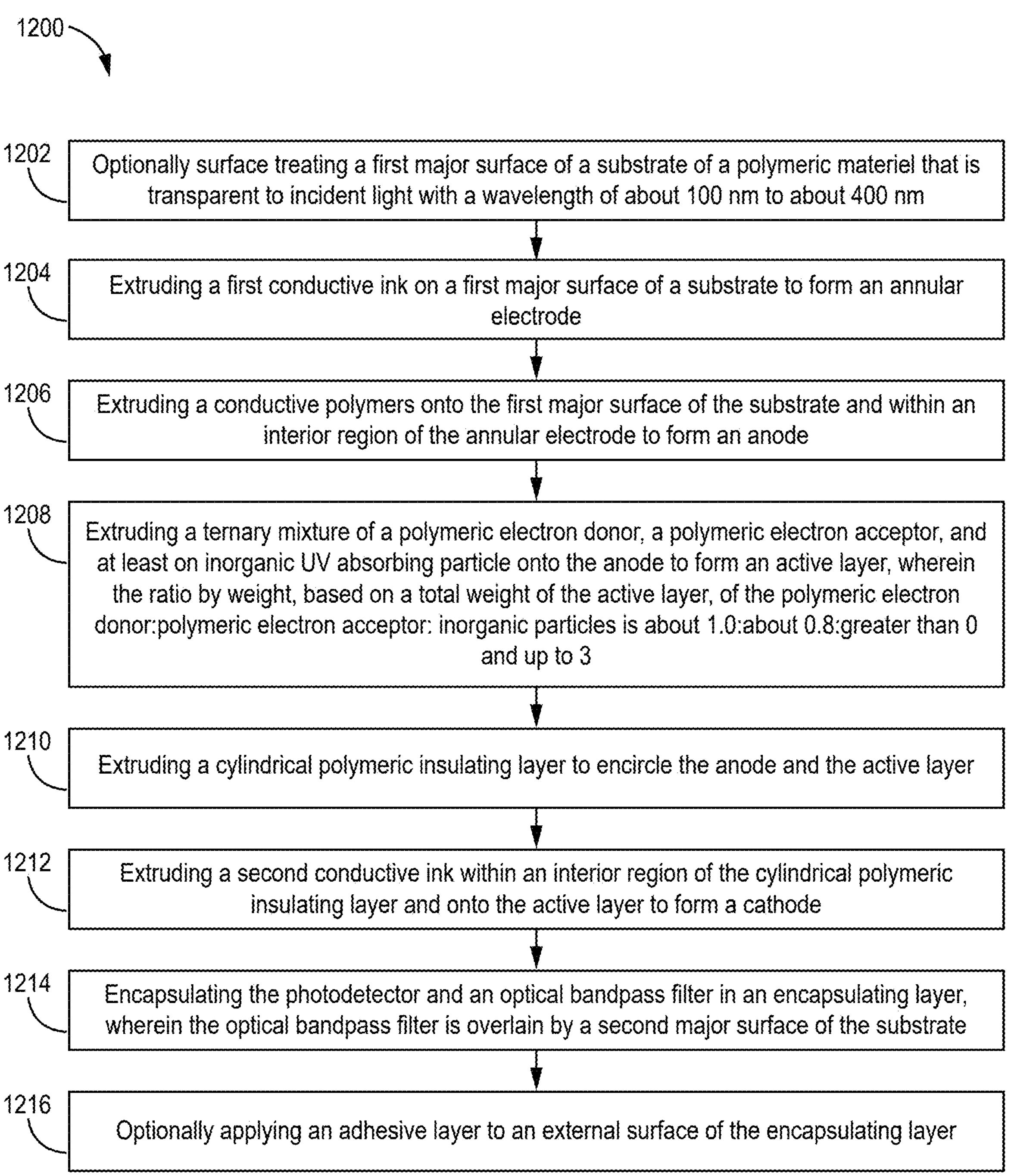
FIG. 8 is a flow chart illustrating an embodiment of a method for making the photodetectors of the present disclosure using a 3D printing process.

Referring now to the flow chart of FIG. 8, an embodiment of a method 1200 for making a 3D printed photodetector is outlined, which is not intended to be limiting and is provided as an example. The method 1200 includes an optional step

1202 of surface treating a first major surface of a substrate of a polymeric material that is transparent to incident light with a wavelength of about 100 nm to about 1000 nm.

Step 1204 includes extruding a first conductive ink on a first major surface of a substrate to form an electrode.

Step 1206 includes extruding a conductive polymer onto the first major surface of the substrate and within an interior region of the electrode to form an anode.

Step 1208 includes extruding a ternary mixture of a polymeric electron donor, a polymeric electron acceptor, and at least one charge carrier trap material onto the anode to form an active layer.

Step 1210 includes extruding an optional insulating layer to maintain separation between the anode and a subsequently printed cathode.

Step 1212 includes extruding a second conductive ink within an interior region of the polymeric insulating layer and onto the active layer to form a cathode.

Step 1214 includes encapsulating the photodetector and an optical filter in an encapsulating layer, wherein the optical filter is overlain by a second major surface of the substrate. In some examples, the optical filter may also be formed using a 3D extrusion process.

Step 1216 includes optionally applying an adhesive layer to at least a portion of an external surface of the encapsulating layer.

In another aspect, the present disclosure is directed to a method for real-time monitoring of optical irradiance in situ on a non-planar or flexible surface such as, for example, the skin of a patient. The method includes applying to the skin of a patient a skin-wearable photodetector module as described above. The photodetector module includes a plurality of photodetectors, each including an active layer between a metal anode and a metal cathode. The active layer includes a ternary mixture of an electron donor, an electron acceptor, and at least one charge carrier trap material. In one example, the charge carrier trap material includes one or a mixture of inorganic UV absorbing particles. In some examples, the ratio by weight, based on a total weight of the active layer, of the polymeric electron donor:polymeric electron acceptor:inorganic particles in the hybrid active layer is about 1.0:about 0.5 to about 1.2:greater than about 0 and up to about 5. Each photodetector in the photodetector module receives an optical input from an associated optical filter, and the photodetectors and the optical bandpass filters are encapsulated within an encapsulating layer of a polymer. The photodetector module is connected to a control console via a flexible connector.

The method further includes monitoring, with the control console, an output of the photodetector module to profile, guide treatment of, mitigate or prevent a photosensitive medical condition. For example, the monitoring can include transmitting wirelessly, data derived from the output of the photodetector module from the control console to a computing device such as a computer, a tablet, a phone, or a combination thereof.

In another aspect, the present disclosure is directed to a method for monitoring optical irradiance on a non-planar surface such as, for example, a selected region of the skin of a patient. The method includes selecting a plurality of optical filters for monitoring the irradiance over a desired wavelength range, wherein each optical filter has a central wavelength in a wavelength rage of about 100 nm to about 1000 nm. In some examples, the optical filters are formed using a three-dimensional (3D) printing process such as 3D extrusion.

The method further includes forming, with a 3D extrusion process, a photodetector over each of the optical filters to form an array with a plurality of photodetectors. The 3D extrusion process includes extruding a first conductive ink on a first major surface of a substrate to form an electrode; extruding a conducting polymer onto the first major surface of the substrate and within an interior region of the electrode to form an anode; extruding a ternary mixture of a polymeric electron donor, a polymeric electron acceptor, and at least one charge carrier trap material to form an active layer. In one example, the charge carrier trap material includes one or a mixture of inorganic UV absorbing particles, wherein the ratio by weight, based on a total weight of the active layer, of the polymeric electron donor:polymeric electron acceptor:inorganic particles is about 1.0:about 0.5 to about 1.2: greater than about 0 and up to about 5. The method further includes extruding a second conductive ink to form a cathode. In some examples, the method further includes extruding a polymeric insulating layer to maintain a separation between the anode and the cathode.

The method further optionally includes encapsulating the photodetectors and the array of optical filters within an encapsulating layer to form a photodetector module, and may optionally include applying an adhesive layer on at least a portion of an external surface of the encapsulating layer of the photodetector module for adherence to the skin of the patient.

The photodetector module may then be adhered to the skin of the patient via the adhesive layer and connected to a control console. The method further includes monitoring, with the control console, an output of the photodetector module to diagnose or treat a medical condition. For example, the monitoring can include wirelessly transmitting data derived from the output of the photodetector module from the control console to a computing device such as a computer, a tablet, a phone, or a combination thereof.

In some examples, the photodetectors of the present disclosure may be rapidly 3D printed in a practitioner's office, and the printed photodetectors may be associated with optical filters selected for monitoring patient skin exposure to specific wavelengths of light. The optical bandpass filters/photodetectors may be arranged in any fashion to form an array, and then encapsulated in an encapsulating layer of a polymer to form a custom photodetector module.

The custom photodetector module may then be adhered to the skin of the patient in a particular area, and electrically connected to the control console for monitoring of light exposure to the selected area of skin. The control console may be used to transmit data to a tablet or a phone, or may be stored in the control console for later analysis by the practitioner.

The photodetector modules of the present disclosure may thus be rapidly produced in an office setting at relatively low cost and personalized for each patient. The modular nature of the components of the photodetection system of the present disclosure, including the photodetector module, the flexible connector, and the control console, make the system readily adaptable to the treatment needs of a wide variety of patients.

In another example, the photodetector modules of the present disclosure, which image the solar spectrum over a desired range of wavelengths, can be an implantable medical device. In one example, the photodetector module can be used as a sensor to replace a human or an animal eye, and in some cases may be configured to be implanted in an orbit of a human cranium. For example, the photodetector module can be made about 20 mm in diameter, which is approximately the same size as a human retina (typically about 30-40 mm in diameter), and with approximately the same thickness as the human retina. In one example, the photodetector module can be built into a compliant and implantable silicone substrate and sealed in an encapsulating layer, and implanted as a replacement for a human eye.

The properties and characteristics of the devices of the present disclosure will now be further illustrated in the following examples.

EXAMPLES

Materials

P3HT (part number 900563), PCBM (part number 684430), ZnO nanoparticles (NPs) (part number 677450), EGaIn (part number 495425), silver paste (part number 735825), PEDOT:PSS solution (0.8 wt %, part number 739316), AgNPs dispersion (30-35 wt %, part number 736465), trichloro(1H,1H,2H,2H-perfluorooctyl) silane (TPFS, part number 448931), chlorobenzene (CB, part number 284513), 1,2-dichlorobenzene (DCB, part number D56802), methanol (MeOH, part number 34860) were ordered from MilliporeSigma, St. Louis, MO. Room temperature-cure silicone (available under the trade designation LOCTITE SI 595 CL) was ordered from Henkel AG & Co., Dusseldorf, DE. A conductive epoxy (8331D-14G) was ordered from MG Chemicals, Ontario, CA. PDMS (available under the trade designation SYLGARD 184) was purchased from Dow Inc., Midland, MI. Silicone adhesive (RT Gel 4317) was obtained from Elkem, East Brunswick, NJ.

Photoactive ink preparation: Solvent 1 resulted from mixing CB and DCB in a 9:1 weight ratio, and Solvent 2 was the mixture of MeOH and DCB in a 9:1 weight ratio. P3HT and PCBM solutions were dissolved in Solvent 1 with concentrations of 30 mg $mL^{-1}$ and 24 mg $mL^{-1}$, respectively. The photoactive material was prepared with an equal weight ratio of P3HT solution and PCBM solution. Then, the binary mixture was diluted with CB to $1/10^{th}$ of the initial concentration, and stirred at 700 rpm for 24 hr. The ZnO NPs dispersion with a concentration of 30 mg $mL^{-1}$ was produced by dispersing ZnO NPs in Solvent 2 followed by ultrasonication for 30 min and stirring at 900 rpm for 1 hr.

The average ZnO NPs size was ca. 36 nm. To prepare 0ZnO, 1ZnO, 2ZnO, and 3ZnO, 0.15 mL Solvent 2; 0.1 mL Solvent 2 and 0.05 mL ZnO NPs dispersion; 0.05 mL Solvent 2 and 0.1 mL ZnO NPs dispersion; and 0.15 mL ZnO NPs dispersion were added into 1 mL diluted P3HT:PCBM solution, respectively. Next, the ternary active material was stirred at 700 rpm for 1 hour.

3D printing of photodetectors: The glass substrate was cleaned by an ultrasonic bath in ethanol for 30 min. The UVO cleaner was used to treat the cleaned glass substrate for 20 min. The UVO-cleaned glass substrate was then silanized with TPFS for a low surface-energy coating, which was beneficial for peeling off the printed flexible photodetector array from the glass substrate. The treated glass substrate was placed in a vacuum chamber with a pump (DTC-41, ULVAC KIKO Inc., Miyazaki, JP), and a container with 50 μL TPFS was placed on the side of the glass. The reaction was conducted for 8 hr, and then the silanized glass substrate was baked for 10 min at 80° C. To produce the PDMS film, a blend containing the precursor and curing agent in a 10:1 weight ratio was made, defoamed in a mixer at 2,200 rpm for 5 min, and then deposited on the silanized glass substrate by a spinner at 600 rpm for 1 min. Then, the PDMS films were baked at 70° C. for 3 hr and treated by UVO for 9 min, modifying the surface for appropriate wettability.

The translation stage (ANT130 Nanopositioning System, Aerotech, Inc., Pittsburgh, PA) and pressure dispenser (Ultimus V, Nordson EFD, Westlake, OH) were used to print photodetectors on the treated PDMS film. The substrate was placed on the X-Y translation stage, while a syringe with the appropriate nozzle (Nordson EFD) connected to the dispenser was mounted on the Z translation stage. Predesigned G-code programs were used to control the printer and dispenser. The detailed printing parameters of each layer are summarized in Table S1, Supporting Information. From the literatures, the viscosities of the AgNPs dispersion, PEDOT:PSS and EGaIn were ca. 15, 11 and 1.99 mPa s, respectively. The two parts of conductive epoxy were blended in a weight ratio of 1:1 and then applied on the pins of the printed electrodes.

Next, the FFC was attached to the pins with conductive epoxy, and a pair of magnetic pads assisted in fixing the FFC and the pins. The conductive epoxy was cured for 2 hours (hr) at room temperature.

Next, the optical filters were placed on the printed photodetector array. Subsequently, the device was encapsulated by PDMS and cured at 70° C. for 3 hr. The silicone adhesive was coated on the encapsulated device. Finally, the 3D printed photodetector array was connected via the FFC.

Design and fabrication of the console: The signal processing board in the console contained eight amplification units, two negative supply units, and one ADC. As shown in the schematics of the amplification unit circuit, there were two operational amplifiers (OPAs) in one amplification chip (SM73307, Texas Instruments, Dallas, TX). The left OPA was used to build a TIA to convert the photocurrent to the voltage signal. Compared to an ordinary resistor for converting current to voltage, the TIA has advantages, including stable gain and a better signal-to-noise ratio. The amplification factor of the TIA was set by a feedback resistance network, i.e., a T-type network. The converted voltage signal then was inputted into a subtractor circuit for subtracting a predefined constant which was close to the dark current signal of the photodetector. Next, the analog voltage signal was converted by an ADC (MCP3208, Microchip Technology) to a digital signal which could be transmitted to the Python-based single-board processor (Raspberry Pi Zero W) via a general-purpose input/output (GPIO) port for further processing. Two CMOS switched-capacitor voltage converters (TL7660, Texas Instruments) were used to perform positive-to-negative supply-voltage conversions. The design of the negative supply was informed by the instruction of the datasheet of the chip. The resistors and capacitors of the circuits were ordered from Digi-Key Electronics. The PCB boards were fabricated by PCBWay Technology.

In the single-board processor, the serial peripheral interface ports on the GPIO header were used to communicate with the custom-built signal processing board, and the inter-integrated circuit ports were used to communicate with the UPS module (PiSugar2). The controlling program was based on Python. The graphic interface of the web page was generated by an open-source Python library (Pyecharts). The web server of the console was based on the open-source Apache Server, and the database server of the console was based on the open-source MariaDB Server.

Statistical Analysis: All experimental data including error bars are represented as the mean±standard deviation. The sample size (n) for experimental data was included in the figure captions. All analyses were performed in OriginLab software available from OriginLab Corp., Northampton, MA.

Figure 2A:
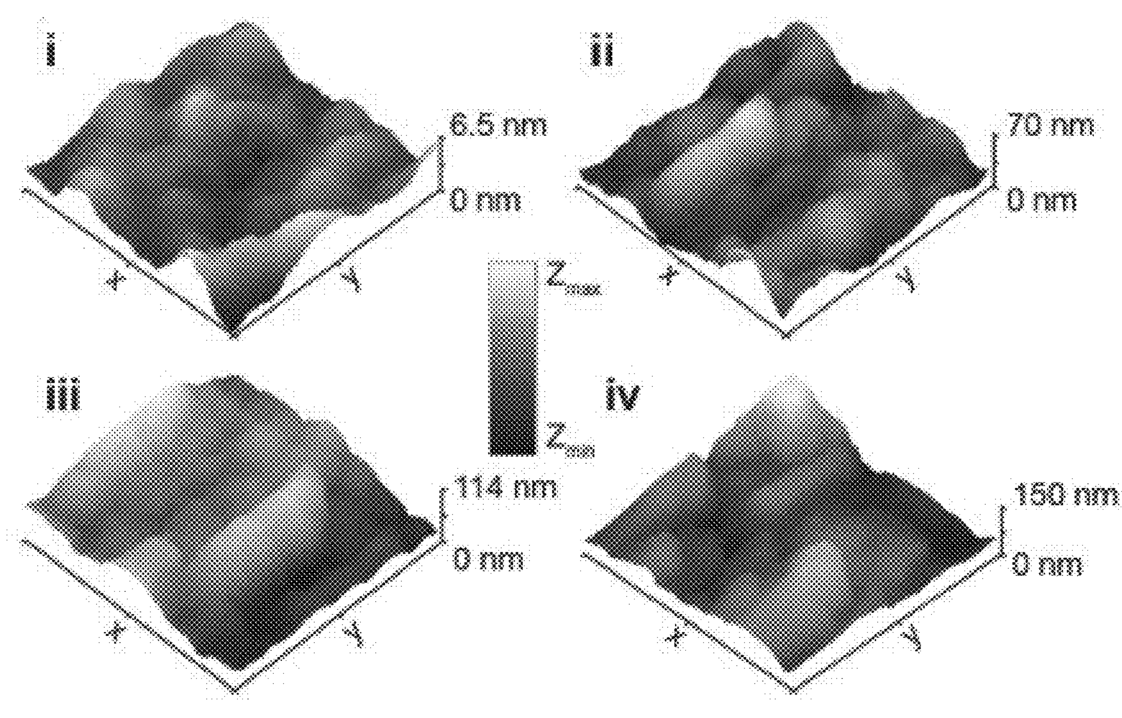
FIG. 2A (i-iv) are atomic force microscopy (AFM) images of active films with 0ZnO (i), 1ZnO (ii), 2ZnO (iii), and 3ZnO (iv) made and tested in the examples of the present disclosure.
Figure 2B:
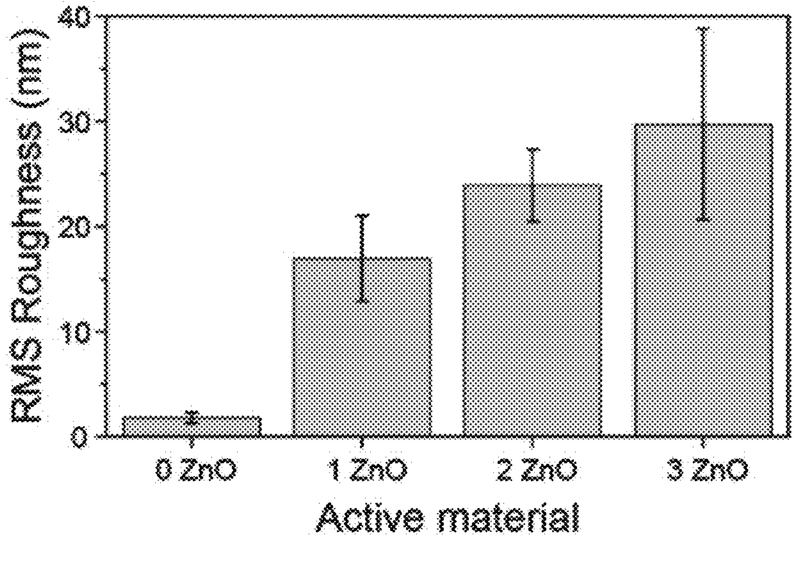
FIG. 2B is a plot of the root mean square (RMS) roughness of films printed with the active materials of FIG. 2A (n=5). The data are presented as mean±SD.

The atomic force microscopy (AFM) images (FIG. 2A) of the active layers (1×1 μm) revealed that the ZnO nanoparticles (NPs) were doped into the organic materials, and the surface roughness increased as the weight ratio of ZnO NPs in the hybrid materials increased (FIG. 2B). The root mean square (RMS) roughness of the photoactive layers printed with the recipes of 0ZnO, 1ZnO, 2ZnO, and 3ZnO were 1.80 nm, 16.95 nm, 23.92 nm, and 29.74 nm, respectively. The increase in the RMS roughness was induced by the large particle size of ZnO relative to the organic molecules, and particle aggregation as the weight ratio of ZnO increased.

Figure 6:
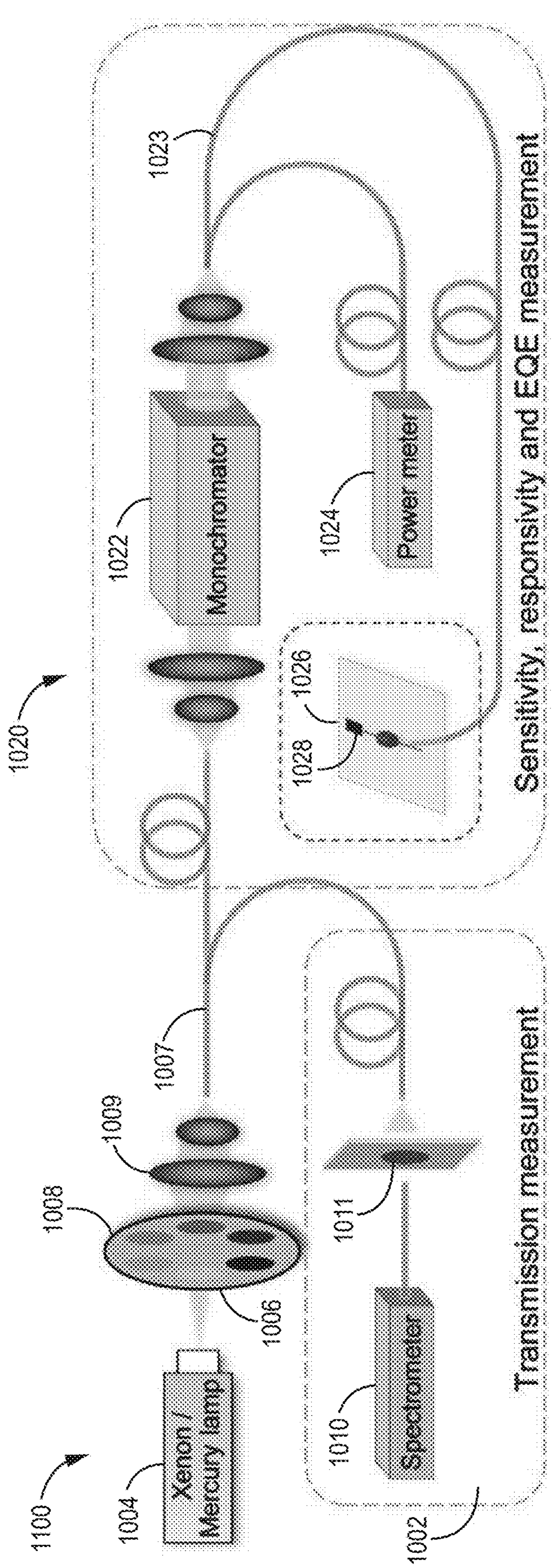
FIG. 6 is a schematic diagram of the test system used in the working examples of the present disclosure.

The optical transmission of the printed active films was characterized with the testing system 1000 shown in FIG. 6, which included a transmission measurement module 1002 and a sensitivity, responsivity, and external quantum efficiency (EQE) measurement module 1020. Each of the modules 1002, 1020 received a test input from a xenon/mercury lamp 1004 available under the trade designation L2174-01 from Hamamatsu Photonics, Bridgewater, NJ), which emitted a broad continuous spectrum light and was used as the light source. A filter wheel 1008 (FWIAND, Thorlabs, Newton, NJ) with neutral density filters 1006 (Thorlabs) was used to adjust the light intensity. The light was then focused and coupled into a bifurcated fiber bundle 1007 (BFY1000HS02, Thorlabs) using two UV-fused silica lenses 1009 (Edmund Optics, Barrington, NJ). The light from one output of the bifurcated fiber bundle illuminated the sample 1011, and the transmission was measured by a UV-Vis spectrometer 1010 (FLAME-S-XR1-ES, Ocean Insight).

In photoresponse measurements, the light source 1004 was a broadband mercury lamp (S1500 without filters, OmniCure, Waltham, MA). The light from another output of the bifurcated fiber bundle was collimated and inputted into a monochromator 1022 (Cornerstone 130, Newport, Irvine, CA). The output light from the monochromator was coupled into a bifurcated fiber bundle 1023, with one output light illuminating the sample and the other monitored by a UV-extended photodiode power sensor (S130VC, Thorlabs, Inc.) connected to an optical power meter 1024 (PM100D, Thorlabs, Inc.). The photoresponse of the sample was then measured by a semiconductor device parameter analyzer (B1500A, Keysight, Santa Rosa, CA). A manual one-axis translational stage 1026 and a laser diode 1028 (CPS405, Thorlabs, Inc.) with neutral density filters was used in the flexibility and stretchability tests.

Figure 2C:
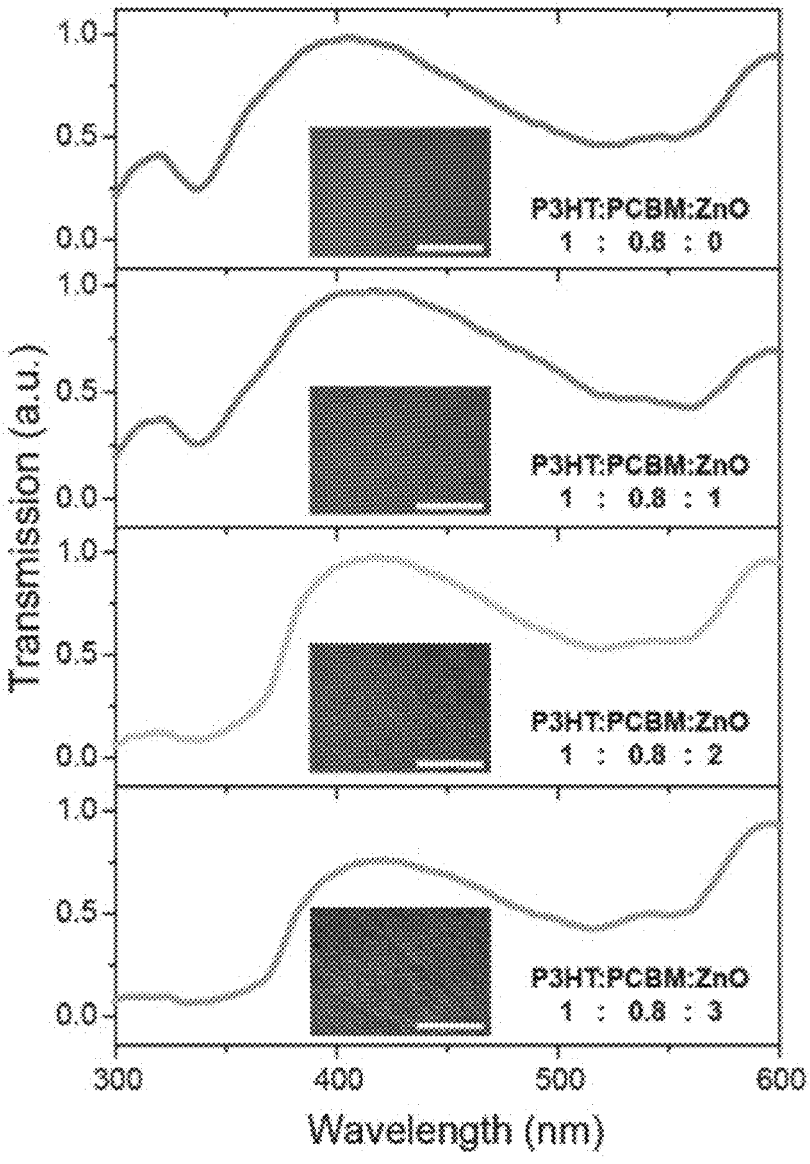
FIG. 2C is a series of plots of normalized transmission spectra of active films made with the active materials of FIG. 2A. The insets are optical microscope images of active films, and the scale bars are 50 microns (μm).

Due to the wide bandgap, ZnO NPs showed a strong UV absorption from 300 nm to 375 nm. The normalized transmission spectrum of the active film with 0ZnO exhibited a small transmission peak and a wide transmission peak at ca. 315 nm and ca. 400 nm (FIG. 2C), respectively. The small transmission peak at 315 nm decreased as the concentration of ZnO NPs in the active materials increased and remained at a low level in both 2ZnO and 3ZnO films, which indicated a strong light absorption in the UVB band. One can also observe a soft cutoff of ca. 375 nm in the transmission spectra of 2ZnO and 3ZnO (see plots 2C1-2C4), which was consistent with the transmission spectrum of ZnO NPs. The optical microscope image of the 3ZnO film showed that the nanoparticle aggregation results in a visible microscale roughness of the active film. Compared with the active film of 2ZnO, 3ZnO had a lower transmission between 400 nm and 560 nm, which may be attributable to the larger scattering and reflection of the rougher active film.

Figure 7:
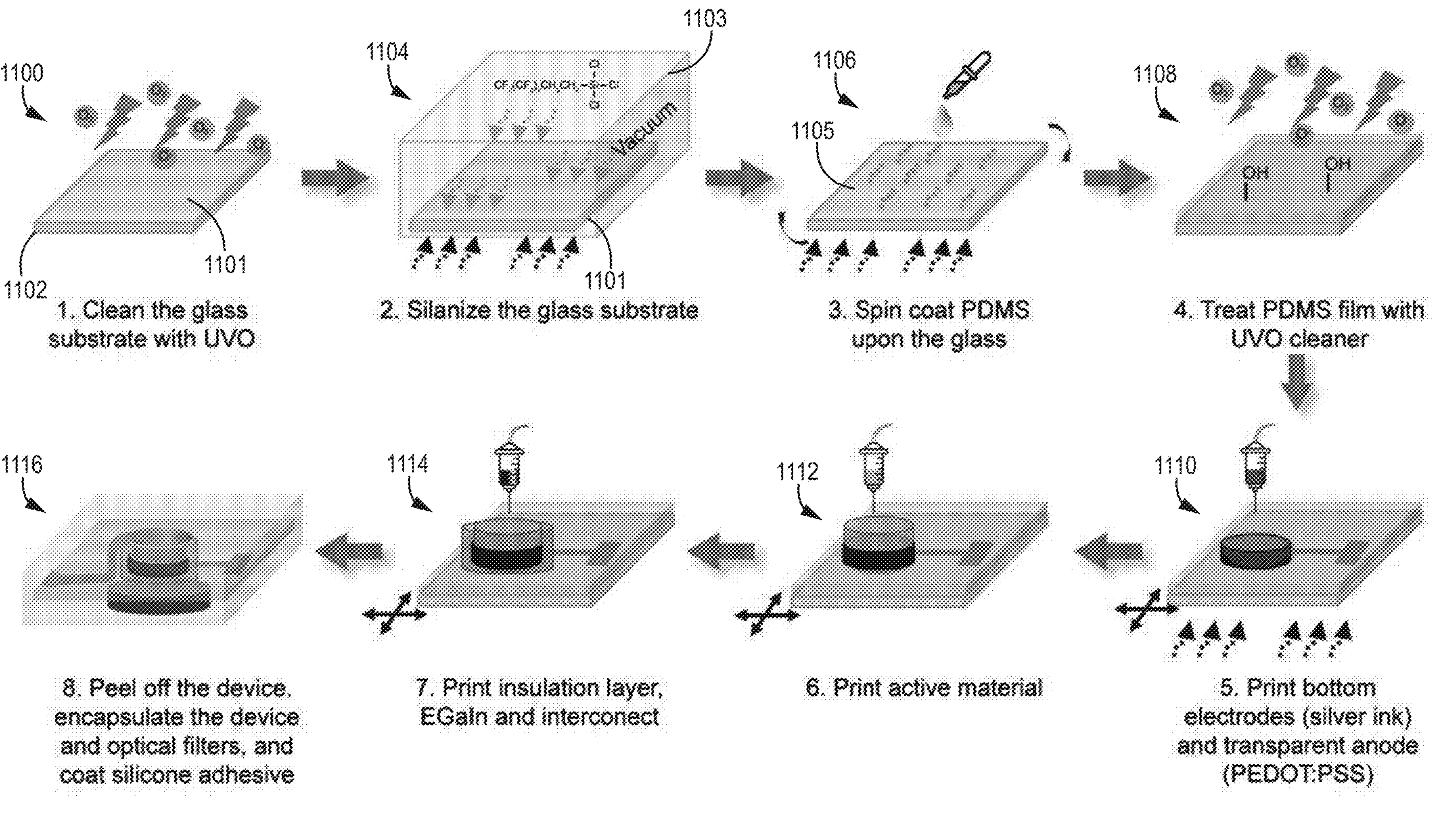
FIG. 7 is a schematic diagram showing a method for making the photodetectors of the present disclosure using a 3D printing process.

Referring now to the schematic diagram in FIG. 7, in a process 1100 for making a photodetector, in step 1102 a glass substrate 1101 was cleaned with an ultraviolet/ozone (UVO) treatment, and in step 1104 the substrate 101 was silanized in a vacuum chamber 1103. In step 1106, a layer 1105 of PDMS was spin coated on the silanized glass. PDMS was chosen as the substrate for the 3D printed photodetectors because of its high transparency in the UV band. The widely used polyethylene terephthalate (PET) is unsuitable for this UV-sensitive application due to its strong light absorption between 300 nm and 340 nm.

Figure 2D:
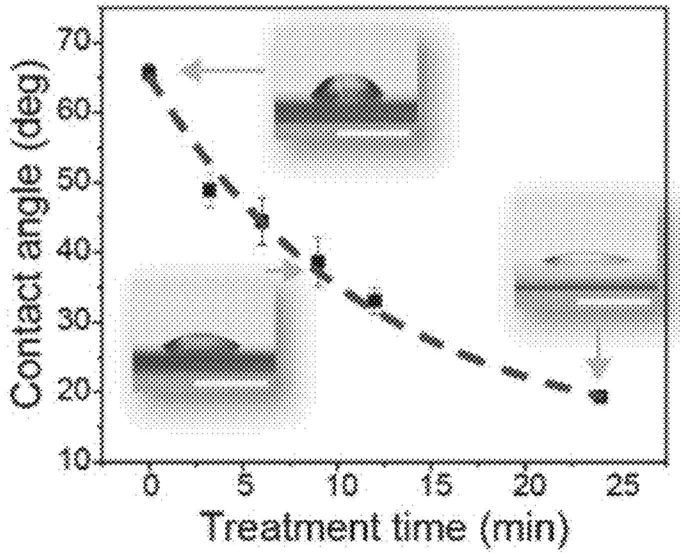
FIG. 2D is a plot showing the dependence of contact angle on UV ozone treatment time (n=5). The insets are images of droplets on the PDMS film, and the scale bars are 1 mm. The data are presented as mean±standard deviation (SD).

In step 1108, UVO treatment, which can cause polymer chain scission and result in polar chemical groups such as Si—OH on the surface of PDMS, was used to improve the wettability of the PDMS substrate prior to printing the silver annular electrodes. The contact angle was measured to assess the wettability (FIG. 2D). The solvent of the silver ink, triethylene glycol monoethyl ether, was used in the characterization of the contact angle. As the UVO treatment period increased from 0 to 24 min, the contact angle decreased from 65.72° to 19.35°, indicating improved wetting of the silver ink solvent on the PDMS surface. Modification of the wettability of the surface of the PDMS substrate provided a more precisely formed 3D printed electrode, because an untreated surface with low surface energy caused the silver ink to form a series of discrete droplets instead of a continuous line. PDMS surfaces with a long 24-minute UVO treatment exhibited an overly small contact angle and prevented the ink from forming precise shapes. As a result, PDMS substrates with a 9-minute UVO-treatment were used in the printing of the photodetectors.

Figure 2E:
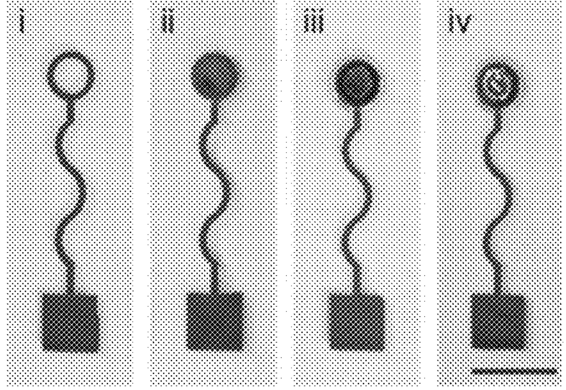
FIG. 2E (i-iv) are photographs of printing steps used to make one photodetector. The scale bar is 5 mm.

With the ability to co-deposit multiple functional materials, 3D printing was used to fabricate the hybrid photodetectors (FIG. 2E, FIG. 7, step 1110). The materials were 3D printed layer-by-layer on the surface of the UVO-treated PDMS films. Printed silver electrodes with a width of ca. 500 μm and thickness of ca. 2.14 μm exhibited a resistivity of $1.04\times10^{-6}\Omega\cdot m$. The circular transparent window of the silver electrode (FIG. 2E-i) was designed to transmit the incident light to the photosensitive layer. The transparent conductive polymer PEDOT:PSS was then printed within the circular window of the silver electrode as the anode of the photodetector. Due to the electron-blocking and hole-transport properties of PEDOT:PSS, this anode layer helped to reduce the dark current of the photodetector. After thermal curing, silver electrodes and PEDOT:PSS layers exhibited shrinkage of ca. 0.43% and 5.11%, respectively. The ternary hybrid active material (FIG. 2E-ii; FIG. 7, step 1112) was then deposited on the PEDOT:PSS layer, and a ring-shaped silicone insulation layer (FIG. 2E-iii) was subsequently printed on the photosensitive layer. Finally, in step 1114, the EGaIn liquid metal (FIG. 2E-iv) was extruded on the predefined photosensitive area as the cathode layer. The insulation layer confined the shape and location of the liquid metal cathode and prevented it from displacing and contacting the silver electrode, avoiding short-circuiting issues.

In FIG. 7, step 1116, the 3D printed photodetector was peeled from the glass substrate and encapsulated, along with an optical bandpass filter, in an encapsulating layer. An adhesive layer was then coated on an external surface of the encapsulating layer.

Figure 3A:
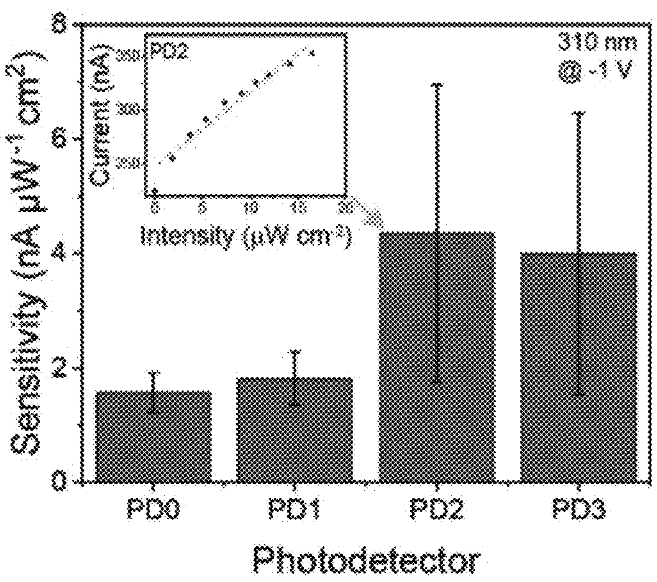
FIG. 3A-C are plots showing the sensitivity of photodetectors with varying active materials of FIG. 2A at a bias voltage of −1 V and wavelengths of A) 310 nm, B) 360 nm, and C) 520 nm, respectively (n=3). The insets in each plot are current-intensity characteristics of the active material composition PD2.
Figure 3B:
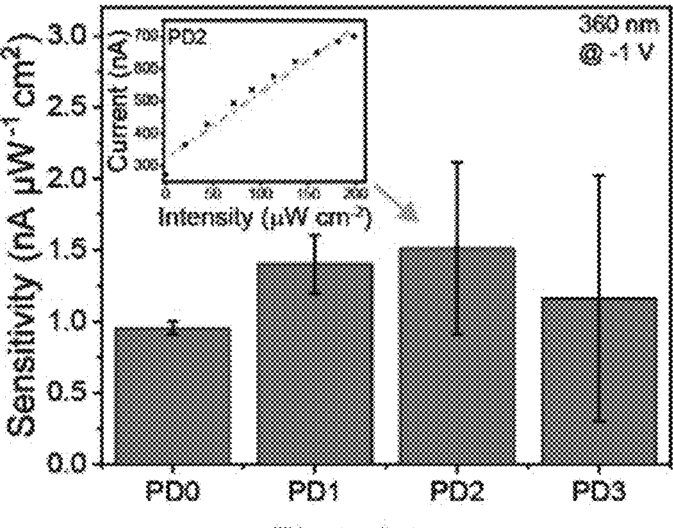
Figure 3C:
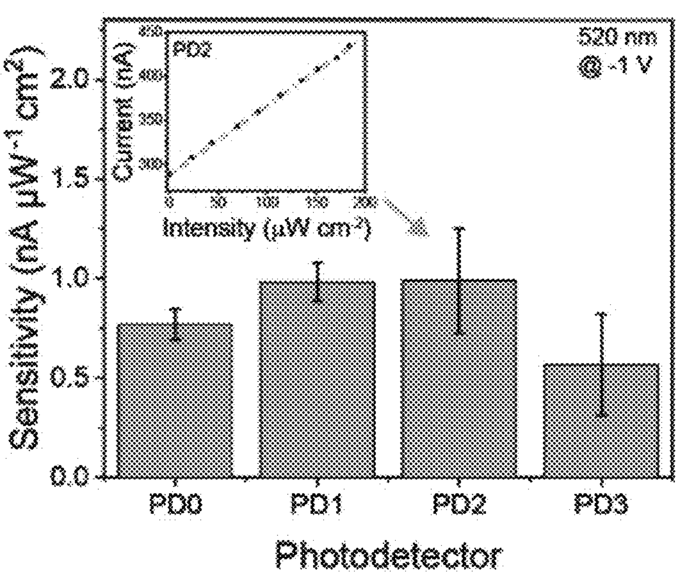

To determine the optimized photoresponse performance, the active material recipes, 0ZnO, 1ZnO, 2ZnO, and 3ZnO, were used to print photodetectors, referenced herein as PD0, PD1, PD2, and PD3, respectively. A linear relationship was observed between the photocurrent and light intensity at a bias of −1 V under irradiation at 310, 360, and 520 nm (FIG. 3A-C insets). The photocurrent and light intensity were then linearly fitted, and the slope of the fitted line was defined as the sensitivity. PD2 showed the highest sensitivities (FIG. 3A-C) among the four types of photodetectors at 310, 360, and 520 nm, with values of 4.4, 1.5, and 0.99 nA $\mu W^{-1}$ $cm^2$, respectively. PD1, PD2, and PD3 showed higher sensitivity than PD0 at 310 nm (FIG. 3A), which indicated that ZnO NPs, the UV absorber, increases the sensitivity at 310 nm. Compared with PD2, PD3 showed lower sensitivity at 310 and 360 nm (FIGS. 3A-B), which, while not wishing to be bound by any theory, might result from the higher surface roughness of the active material with 3ZnO, which impacts the photoresponse performance by causing higher recombination rates. PD1 and PD2 showed higher sensitivities at 520 nm than PD0 (FIG. 3C), even though the ZnO NPs increase surface roughness and do not exhibit a strong absorption in the visible band. The higher sensitivity is thus attributable to PM caused by ZnO NPs in the hybrid active materials.

The responsivity, which measures the electrical output per optical input, is a characteristic used to analyze the photoresponse of the photodiodes. The responsivity (R) of the photodetectors is given by:

$$R = \frac{I_{light} - I_{dark}}{P_{irradiation}}, \quad (1)$$

in which $I_{light}$ and $I_{dark}$ are the currents under irradiation at a certain wavelength and in a dark environment, respectively, and $P_{irradiation}$ represents the incident light power. The shapes of the responsivity spectra (FIG. 3D) corresponded to the transmission spectra of the active layer, which indicated that the photoresponse originated from the hybrid active material. As shown in the responsivity of PD2, the broad peak of the responsivity spectra in the UV range (300-360 nm) and the dip at around 400 nm were consistent with the absorption peak in the UV range and transmission peak at around 400 nm, respectively. PD2 showed the highest responsivities among the photodetectors at 310, 360, and 520 nm, with values of 0.51, 0.2, and 0.09 A $W^{-1}$, respectively. With a greater weight ratio of ZnO NPs with charge traps to trigger a substantial PM effect, PD2 showed enhanced responsivity compared to PD0 and PD1. Moreover, the active layer of PD2 bad a lower surface roughness than PD3, leading to an improved photoresponse, which was consistent with the sensitivity characterization. These responsivity values in fully 3D printed hybrid photodetectors are comparable to those of commercial silicon-based photodetectors (~0.2 A $W^{-1}$).

The EQE is another representative performance indicator, which estimates the ability of the photodetectors to convert incident photons to current. The EQE is calculated according to:

$$EQE = \frac{hcR}{q\lambda}, \quad (2)$$

where R is responsivity, $\lambda$ is wavelength, h represents Planck's constant, c represents the speed of light, and q is the elementary electronic charge. The EQE curves (FIG. 3E) were consistent with the transmission spectra of the active films and the responsivity of the photodetectors. The EQE of PD2 from 300 to 340 nm was above 100%, presumably due to the PM effect. For PD0, the organic materials absorbed the incident photons and generated excitons. The holes and electrons from photogenerated excitons moved from the highest occupied molecular orbital (HOMO) and lowest unoccupied molecular orbital (LUMO) of the active material, to the transparent PEDOT:PSS anode and the EGaIn cathode through the PCBM layer, respectively. Due to the energy level difference, there was a larger injection barrier between the EGaIn (ca. 4.3 eV) and HOMO of the organic active materials (P3HT with ca. 5.2 eV and PCBM with ca. 6.1 eV), which prevented the holes from injecting into the active area. For the hybrid photodetector, the photogenerated electrons were trapped in the ZnO of the active layer instead of directly transmitting to the cathode, because of the surface defects on the NPs. The trapped electrons in ZnO NPs acted as space charges to produce a Coulomb field, which induced band bending near the cathode layer, which improved the hole tunneling injection by reducing the injection barrier and therefore resulted in the PM effect. Subsequently, the holes from the external circuit were transmitted to the P3HT and transported together with photoinduced holes towards the PEDOT:PSS anode, which formed the enhanced photocurrent signal. As discussed previously, due to this hole tunneling injection, the EQE of photodetectors exhibiting the PM effect can be larger than 100%. With a bias of −1 V, PD2 showed the highest EQE of 203.5% at 310 nm, 68.97% at 360 nm, and 22.18% at 520 nm among the four types of photodetectors. Because a higher bias voltage is needed for charge carriers to overcome energy barrier, the EQE increased rapidly as the bias voltage increased by allowing more charge carriers to overcome the energy barrier.

The specific detectivity (D*) describes the ability of the photodetectors to sense faint light intensities, and can be calculated and characterized using equation (3) as:

$$D^* = \frac{R\sqrt{A}}{\sqrt{2qI_{dark}}}, \quad (3)$$

where R is the responsivity, A is the active area of the photodetector, and $I_{dark}$ is the dark current.

The specific detectivities of PD2 were $2.49\times10^{11}$, $9.21\times10^{10}$, and $3.62\times10^{10}$ cm $Hz^{1/2}$ $W^{-1}$ at 310, 360, and 520 nm, respectively. PD2 showed the highest specific detectivity in the spectral band ranging from 300 nm to 360 nm, while PD1 showed higher specific detectivity in the 370-650 nm range (FIG. 3F). PD1 exhibited higher specific detectivity in the visible band than PD2 because PD1 showed similar responsivity, and the dark current was lower due to the smoother active films.

Figures 4A, 4B, 4C:
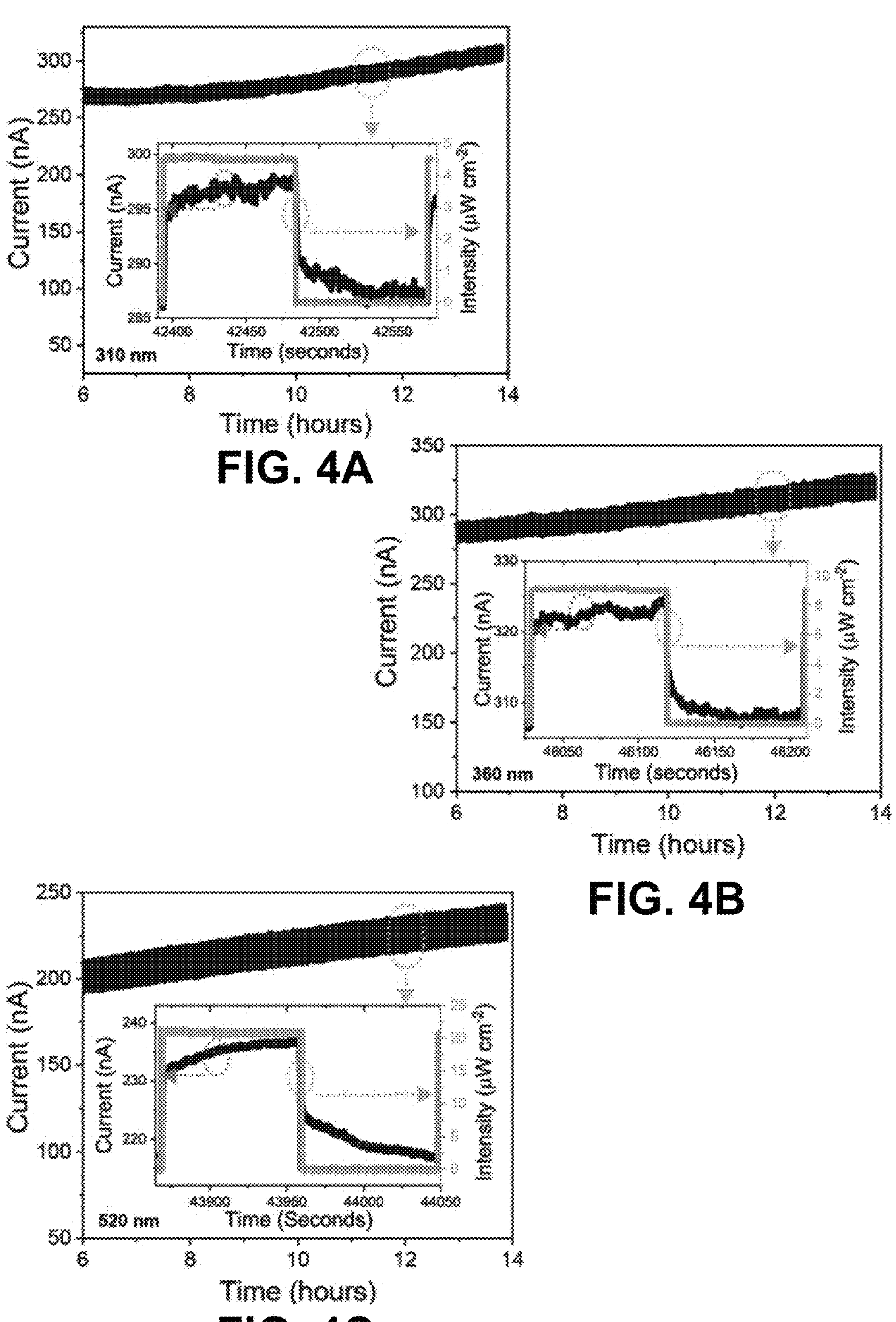
FIGS. 4A-C are plots showing the current response of a photodetector to 310 nm, 360 nm, and 520 nm on/off modulated light, respectively, in the last 8 hours of a test period of 14 h. The light intensities used in FIGS. 4A-C are ca. 4.6, 9.2, and 21.1 μW cm 2, respectively. The insets in FIGS. 4A-C are magnified views of current responses.

Due to its high performance in terms of sensitivity, responsivity, and EQE in the broadband, PD2 was selected for the wearable photodetector in the light intensity monitoring system. The electrical stability of PD2 was investigated under long-term on-off modulated illumination (FIGS. 4A-C). Decays in the dark current and photocurrent were observed during the first 6 hours of the electrical stability test period. While not wishing to be bound by any theory, this reduction in current may result from the degradation of the polymer active material, which is common in organic optoelectronic devices. After 6 hours, the current, including the dark current and photocurrent, increased over time, which might result from the persistent photoconduction phenomenon. This is caused by accumulated electrons in ZnO NPs due to the slow oxygen adsorption and desorption rate on ZnO surfaces. The response time (FIGS. 4A-C, insets) included a fast transient (<0.1 s) followed by a slow rise (>10 s), which indicated that the photoresponse resulted from polymers and nanoparticle active materials. The rise times of the photodetector under the illumination of 310, 360, and 520 nm were 34.9, 26.4, and 30.2 seconds, respectively.

Figure 4D:
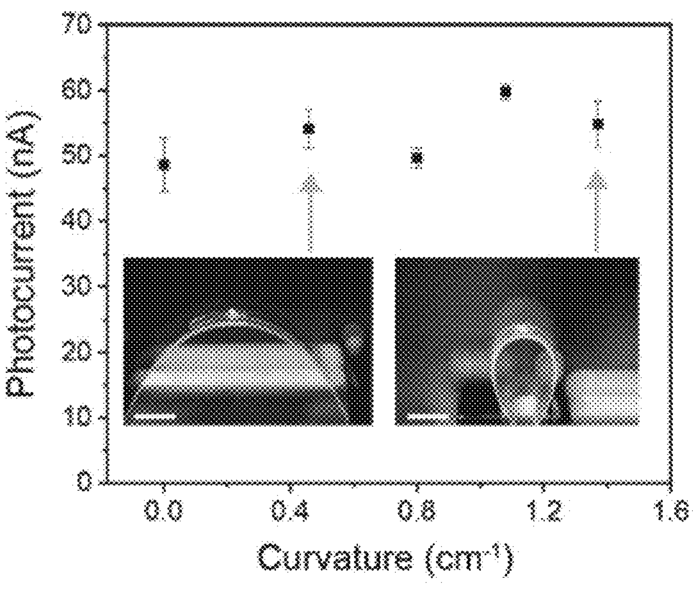
FIG. 4D is a plot of the photocurrent of a photodetector under a bending test (n=5). The left and right insets are photographs of the photodetector undergoing curvatures of 0.46 and 1.37 $cm^{-1}$, respectively. The scale bars are 10 mm, the data are presented as mean±SD.

The flexibility of the photodetector module was characterized by attaching the device to a PET film and mounting it on a translation stage to adjust the bending curvature (FIG. 4D insets). The bent photodetector was illuminated from the bottom side by a 405 nm laser diode. The light intensity of the laser was 47.46 $\mu W\ cm^{-2}$. The photodetector showed stability under mechanical bending (FIG. 4D) and cyclic bending tests, showing no significant change in the photoresponse as the bending curvature changed due to the flexibility of the organic materials. The photocurrent output of the photodetector module may only vary a small amount, such as no more than about ±10 μA when the module is at a curvature of up to about 1.5 $cm^{-1}$. In some examples, as shown in the plots in FIG. 4D, the photocurrent output of the photodetector module varied no more than about ±10 nA when the module was at a curvature of up to about 1.5 $cm^{-1}$. However, larger devices operating under larger current may have a corresponding higher variation in current.

Figure 4E:
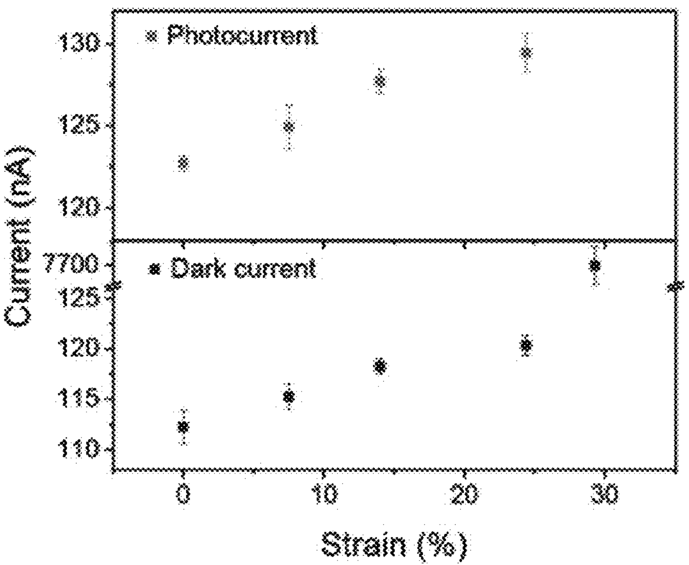
FIG. 4E is a plot of photocurrent and dark current of the photodetector at varying tensile strains (n=5). The data are presented as mean±SD.

To characterize the stretchability, the photodetector module was fixed on a one-axis translation stage, and then strain was applied. The same laser diode was used in the stretchability test and the flexibility test. When strain increased on the photodetector, the photocurrent and the dark current increased (FIG. 4E). While not wishing to be bound by any theory, this phenomenon might result from the proportional relationship between the sheet resistance of the active film and the thickness, which decreases under strain. Moreover, the change of reverse bias injection-limited current (I) can be predicted by $I \alpha\ V/T$, with V as the voltage and T as the thickness of the layer. The proportion of V to T represents the effective electric field in the photosensitive layer, such that a larger effective electric field assists the charges to overcome the injection barrier and increase the current. The photocurrent and dark outputs of the photodetector module may only vary a small amount, such as no more than about ±10 μA when the module is subjected to a tensile strain of up to about 30%. In some examples, as shown in the plots in FIG. 4E, the photocurrent and dark current outputs of the photodetector module varied no more than about ±10 nA when the module was subjected to a tensile strain of up to about 25%. However, larger devices operating under larger current may have a corresponding higher variation in current.

Figure 4F:
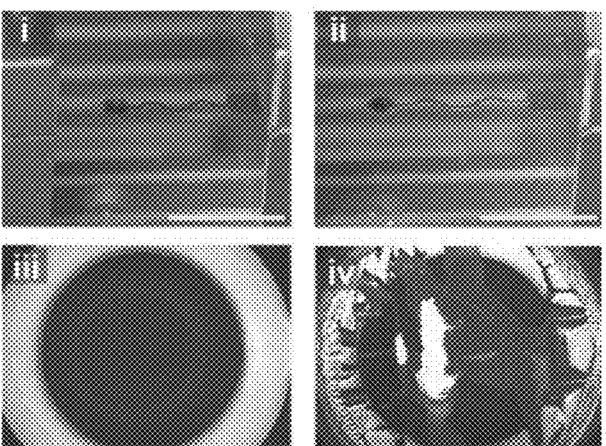
FIG. 4F (i-iv) is a series of photographs showing a photodetector under 0% (i) and 29.3% (ii) strain, respectively. The scale bars are 10 mm. The photographs (iii) and (iv) are optical microscope images of the sensing areas in (i) and (ii), respectively. The scale bars are 1 mm.

The dark current at the strain of 29.3% experienced a sharp rise and reached a value of ca. 7.53 μA because the active layer and transparent anode were damaged under the strain, through which the liquid metal cathode leaked into the anode and caused a short circuit (FIG. 4F). The white spots in the sensing area showed liquid metal leakage, indicating short-circuiting of the photodetector. As the transparent anode and active layer in the sensing area were vulnerable to tensile strain, the circular-shaped electrode was designed for the sensing area to reduce the extension of the anode and active layer under tensile strain. The cracks along the y-axis in the central sensing area resulted from the stress along the x-axis, while the wrinkles along the x-axis in the silver electrode were caused by the stress along the y-axis. The wrinkles also indicated that some parts of the electrode delaminated from the PDMS substrate during the tensile testing.

Figure 5A:
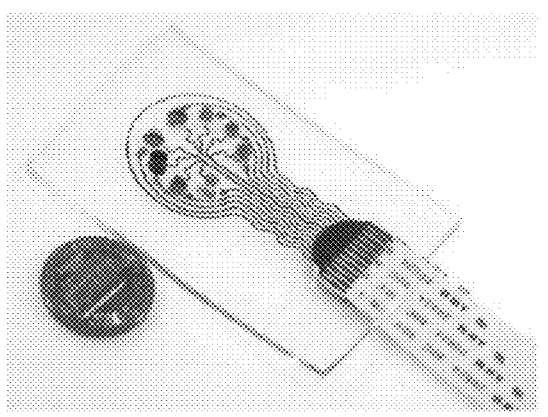
FIG. 5A is a photograph of a photodetector module of the present disclosure as connected to a flexible cable. The photodetector module included 8 photodetectors, each associated with an optical bandpass filter for monitoring the light intensity of eight different wavelengths.
Figure 5B:
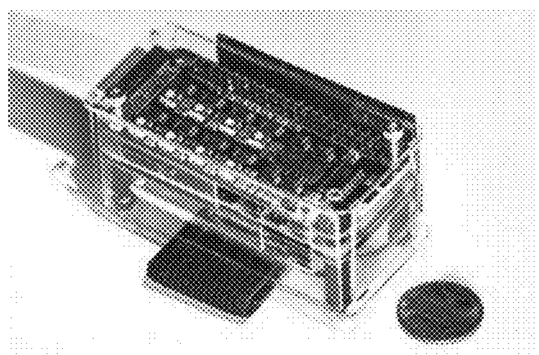
FIG. 5B is a photograph of the control console of the photodetection system of the present disclosure showing a signal processing board, a single-board processor, and an uninterruptable power supply (UPS) module.
Figure 5C:
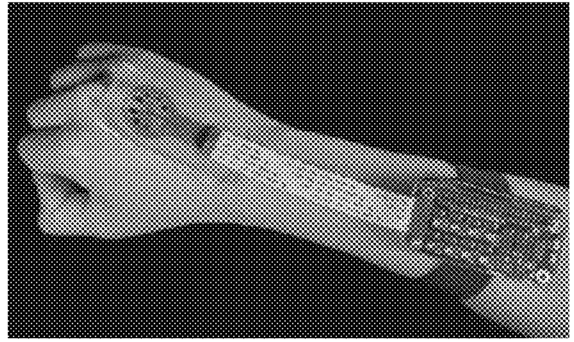
FIG. 5C is a photograph of the photodetector module of FIG. 5A and the control console of FIG. 5B attached to a human hand for in-situ light intensity monitoring.

The encapsulated 3D printed photodetector array (including the active layer formulation PD2) with eight optical filters (FIG. 5A) was connected to a customized electrical console (FIG. 5B) via a flat flexible cable (FFC). The photodetector array was 3D printed layer-by-layer on the PDMS film. The thicknesses of anode layer, active layer, silicone insulation layer and conductive interconnect were measured to be 288.43±80.25 nm, 226.78±74.85 nm, 60.41±1.35 μm, and 42.22±1.58 μm (n≥3), respectively. The projected area of the console was smaller than a credit card, which made it viable to serve as a wearable device. The system could be powered by a lithium battery and charged by a solar cell or a commonly used 5 V charger due to the low bias voltage operation of the 3D printed hybrid photodetectors. By coating the device with a silicone adhesive, the system could be firmly attached to the arm (FIG. 5C). The central wavelength of eight bandpass optical filters in the 3D printed photodetector array ranged from 310 to 650 nm.

Figure 5D:
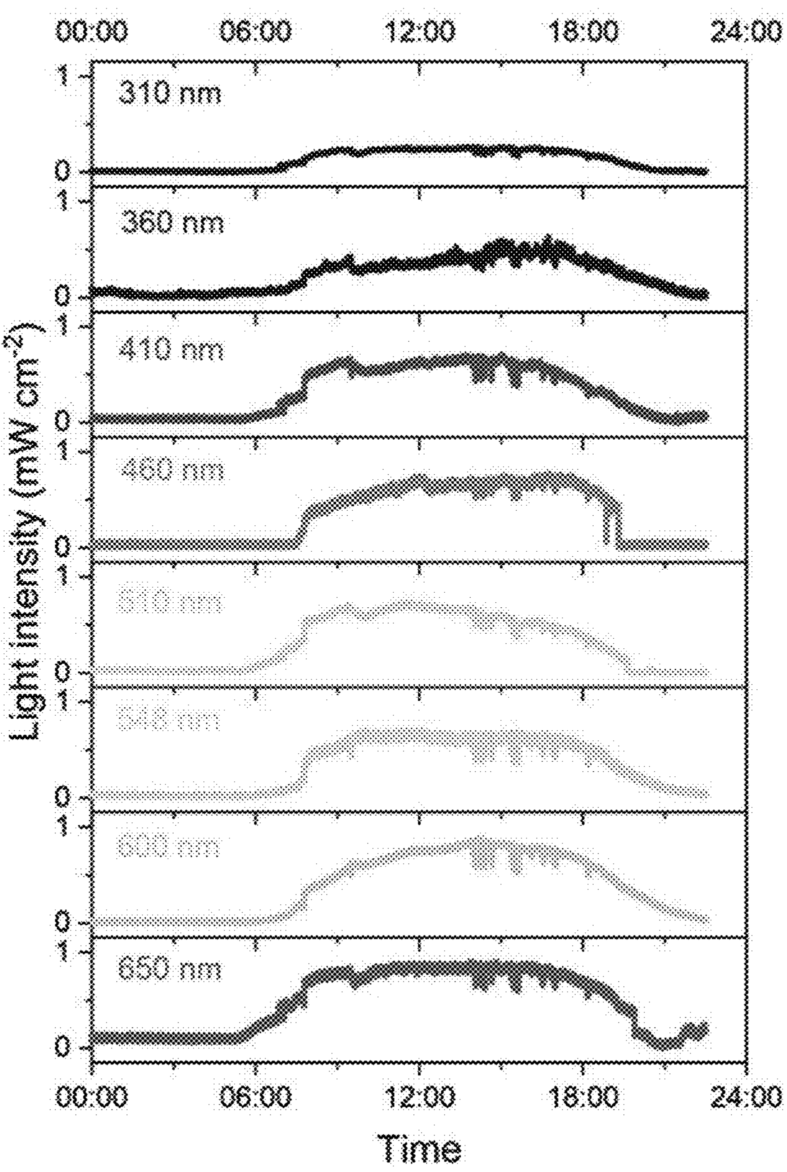
FIG. 5D is a series of plots showing the light intensity, measured by the monitoring system, of eight different wavelengths ranging from UVB to the visible band of natural sunlight during a full day in Minneapolis, Minnesota, on May 12, 2021.

In addition to the tests in the laboratory, an outdoor test recorded the light intensity distribution for nearly 24 hours in Minneapolis, Minnesota, on May 12, 2021, using the monitoring system. The system was exposed to natural sunlight and continuously recorded the light intensity with a time interval of ca. 1 s. The light intensities (FIG. 5D) generally increased after sunrise (ca. 06:00) and decreased gradually until sunset (ca. 20:30). The fluctuations of the distribution of light intensity after 12:00 correspond to passing cloud cover. A multifunctional web server with a graphical interface was developed and executed on the monitoring system to allow facile access to the light intensity data. The figures for the light intensity distribution could be generated and downloaded via a wireless connection, rendering it convenient for physicians and users to continuously monitor environmental light exposure.

Example 1: A skin-wearable photodetector module includes an array includes a plurality of photodetectors; and a plurality of optical filters, wherein each photodetector of the plurality of photodetectors is configured to receive an optical input from an optical filter of the plurality of optical filters having a central wavelength in a wavelength range of about 100 nm to about 1000 nm, and wherein each photodetector comprises: a substrate defining a first major surface and a second major surface, wherein the second major surface overlies a corresponding optical filter of the plurality of optical filters; an electrode overlying the first major surface of the substrate and defining an interior region; an anode within the interior region of the electrode; an active layer overlying the anode and comprising a ternary mixture of an electron donor, an electron acceptor, and at least one charge carrier trap material; and a cathode overlying the active layer.

Example 2: The photodetector module of example 1, wherein each of the photodetectors of the plurality of photodetectors and a corresponding optical filter of the plurality of optical filters are within an encapsulating layer of a polymer.

Example 3: The photodetector module of any of examples 1 and 2, wherein the charge carrier trap material in the active layer is chosen from inorganic ultraviolet (UV)-absorbing nanoparticles, quantum dots, organic dyes, and mixtures and combinations thereof.

Example 4: The photodetector module of example 3, wherein the charge carrier trap material comprises inorganic UV-absorbing particles.

Example 5: The photodetector module of example 4, wherein the active layer comprises a ratio by weight, based on a total weight of the active layer, of: about 1.0 parts of polymeric electron donor:about 0.5 to about 1.2 parts of a polymeric electron acceptor:greater than about 0 parts and up to about 5 parts of inorganic UV-absorbing nanoparticles.

Example 6: The photodetector module of any of examples 4 and 5, wherein the active layer comprises a ratio by weight, based on a total weight of the active layer, of: about 1.0 parts of polymeric electron donor:about 0.8 parts of a polymeric primary electron acceptor:greater than about 0 parts and up to about 3 parts of inorganic UV-absorbing nanoparticles.

Example 7: The photodetector module of any of examples 4 through 6, wherein the inorganic UV-absorbing nanoparticles are chosen from ZnO, TiO2, CeO2, and mixtures and combinations thereof.

Example 8: The photodetector module of example 7, wherein the inorganic UV-absorbing nanoparticles comprise ZnO.

Example 9: The photodetector module of any of examples 7 and 8, wherein the inorganic UV-absorbing nanoparticles consist essentially of ZnO.

Example 10: The photodetector module of any of examples 1 through 9, further comprising an insulating layer separating the anode and the cathode.

Example 11: The photodetector module of example 10, wherein the insulating layer has a cylindrical shape, and wherein the insulating layer encircles the anode and the active layer within an interior region of the cylindrical insulating layer.

Example 12: The photodetector module of any of examples 2 through 11, wherein an external surface of the encapsulating layer comprises an adhesive layer.

Example 13: The photodetector module of any of examples 1 through 12, wherein the photodetectors are circumferentially arranged.

Example 14: The photodetector module of any of examples 1 through 13, wherein each of the optical filters has a central wavelength that differs by about 50 nm to about 100 nm over the wavelength range.

Example 15: The photodetector module of any of examples 2 through 14, further comprising a connector circuit encapsulated in the encapsulating layer and electrically coupled to the electrode.

Example 16: The photodetector module of example 15, wherein the connector circuit comprises an arrangement of serpentine electrodes.

Example 17: The photodetector module of any of examples 1 through 16, wherein the module is sufficiently stretchable such that a photocurrent and a dark current produced by the module varies no more than about ±10 μA under a tensile strain of up to about 30%.

Example 18: The photodetector module of any of examples 1 through 17, wherein the module is sufficiently flexible such that a photocurrent produced by the module varies no more than about ±10 μA at a curvature of up to about 1.5 $cm^{-1}$.

Example 19: The photodetector module of any of examples 1 through 18, wherein the module has an external quantum efficiency (EQE) of greater than 100% at a wavelength range greater than 100% at a wavelength range of 310-650 nm at a bias voltage of −1 V.

Example 20: The photodetector module of any of examples 2 through 19, wherein the encapsulating layer and the substrate each comprise polydimethylsiloxane (PDMS).

Example 21: The photodetector module of any of examples 1 through 20, wherein the substrate comprises a polymeric material that is transparent to incident light with a wavelength of about 100 nm to about 1000 nm.

Example 22: The photodetector module of any of examples 1 through 21, wherein the first major surface of the substrate comprises a modified surface, and wherein the modified surface has enhanced wettability to an anode material.

Example 23: The photodetector module of any of examples 1 through 22, wherein the anode comprises a conducting or semiconducting polymer.

Example 24: The photodetector module of example 23, wherein the polymer comprises poly(3,4-ethylenedioxythiophene):polystyrene sulfonate (PEDOT:PSS).

Example 25: The photodetector module of any of examples 1 through 24, wherein the electron donor comprises a polythiophene.

Example 26: The photodetector module of example 25, wherein the polythiophene comprises poly(3-hexylthiopene) (P3HT).

Example 27: The photodetector module of any of examples 1 through 26, wherein the electron acceptor comprises a functionalized fullerene.

Example 28: The photodetector module of example 27, wherein the functionalized fullerene comprises 6,6 phenyl C61-butyric acid methyl ester (PCBM).

Example 29: The photodetector module of any of examples 1 through 28, wherein the cathode comprises a metal chosen from EGaIn, Ag, Au, Cu, and mixtures and alloys thereof.

Example 30: The photodetector module of example 29, wherein the cathode comprises EGaIn.

Example 31: The photodetector module of example 30, wherein the cathode comprises a mixture of EGaIn and a polymeric modifier.

Example 32: The photodetector module of any of examples 1 through 31, wherein the electrode comprises a conductive metal.

Example 33: The photodetector module of example 32, wherein the conductive metal is chosen from Ag, Au, Cu, and mixtures and alloys thereof.

Example 34: The photodetector module of any of examples 1 through 33, wherein each optical filter of the plurality of optical filters comprises a device, membrane, or coating configured to selectively transmit light of a selected wavelength.

Example 35: A photodetection system configured for removable attachment to human skin includes a skin-wearable photodetector module includes an array includes a substrate defining a first major surface and a second major surface, wherein the substrate comprises a polymeric material that is transparent to incident light with a wavelength of about 100 nm to about 1000 nm, and wherein the second major surface of the substrate is adjacent to a corresponding optical filter of the plurality of optical filters; a metal electrode overlying the first major surface of the substrate and includes about 1.0 parts of polymeric electron donor: about 0.5 parts to about 1.2 parts of a polymeric primary electron acceptor:greater than about 0 parts and up to about 5 parts of UV absorbing inorganic particles; a connector circuit electrically coupled to the metal electrode; and an encapsulating layer encapsulating the plurality of photodetectors, the plurality of optical filters, and the connector circuit; a connector electrically coupled to the connector circuit; and a control console connected to the connection circuit, wherein the control console comprises a signal processing module, a data processing module, and a power supply.

Example 36: The photodetection system of example 35, wherein the power supply comprises a battery, and wherein the power supply provides power sufficient to operate the photodetection system for at least 24 hours.

Example 37: The photodetector system of example 36, wherein the power supply further comprises a solar cell.

Example 38: The photodetection system of any of examples 35 through 37, wherein the data processing module comprises a processor and a memory.

Example 39: The photodetection system of example 38, wherein the processor comprises the memory.

Example 40: The photodetection system of any of examples 38 and 39, wherein the processor is connected to a database.

Example 41: The photodetection system of any of examples 35 through 40, wherein the data processing module further comprises a wireless module.

Example 42: The photodetection system of any of examples 35 through 41, wherein the signal processing module is configured to supply a bias voltage to the photodetector module.

Example 43: The photodetection system of any of examples 35 through 42, wherein the connector circuit comprises an arrangement of serpentine electrodes.

Example 44: The photodetection system of any of examples 35 through 43, wherein the connector comprises a flat flexible cable.

Example 45: The photodetection system of any of examples 35 through 44, wherein an external surface of the encapsulating layer comprises thereon an adhesive layer.

Example 46: The photodetection system of any of examples 35 through 45, wherein the inorganic particles consist essentially of ZnO, and wherein the active layer comprises the ratio by weight, based on the total weight of the active layer, of about 1.0 parts of a polymeric electron donor:about 0.8 parts of a polymeric electron acceptor:about 1.0 parts to about 2.5 parts of inorganic particles.

Example 47: The photodetection system of any of examples 35 through 46, wherein the inorganic particles consist essentially of ZnO, and wherein the active layer comprises the ratio by weight, based on the total weight of the active layer, of about 1.0 parts of a polymeric electron donor:about 0.8 parts of a polymeric electron acceptor:about 1.0 parts to about 2.0 parts of inorganic particles.

Example 48: A method of making a photodetector with a three-dimensional (3D) extrusion process includes extruding a first conductive ink on a first major surface of a substrate to form an electrode, wherein the substrate comprises a polymeric material that is transparent to incident light with a wavelength of about 100 nm to about 1000 nm, and wherein the electrode defines an interior region; extruding a conducting or semiconducting polymer onto the first major surface of the substrate and within the interior region of the electrode to form an anode; extruding a ternary mixture of a polymeric electron donor, a polymeric electron acceptor, and a charge carrier trap material onto the anode to form an active layer; and extruding a second conductive ink onto the active layer to form a cathode.

Example 49. The method of example 48, further comprising positioning an optical filter on a second major surface of the substrate to provide an optical input to the photodetector, wherein the optical filter has a central wavelength of about 100 nm to about 1000 nm.

Example 50: The method of example 49, further comprising extruding the optical filter onto the second major surface of the substrate.

Example 51: The method of any of examples 48 through 50, wherein the charge carrier trap material in the active layer comprises UV absorbing particles, and wherein the active layer comprises a ratio by weight, based on a total weight of the active layer, of: about 1.0 parts of polymeric electron donor:about 0.5 parts to about 1.2 parts of a polymeric primary electron acceptor:greater than about 0 parts and up to about 5 parts of inorganic particles.

Example 52: The method of any of examples 48 through 51, further comprising extruding an insulating layer between the anode and the cathode.

Example 53: The method of example 52, wherein the insulating layer has a cylindrical shape, and wherein the anode and the active layer are within an interior region of the insulating layer.

Example 54: The method of any of examples 48 through 53, further comprising surface treating at least a portion of the first major surface of the substrate prior to extruding the first conductive ink thereon.

Example 55: The method of example 54, wherein the surface treating comprises applying at least one of a UV-ozone (UVO) treatment or a plasma treatment to at least a portion of the first major surface.

Example 56: The method of any of examples 54 and 55, wherein the surface treating comprises applying a coating to at least a portion of the first major surface of the substrate.

Example 57: The method of any of examples 48 through 56, further comprising sealing the photodetector and the optical filter within an encapsulating layer.

Example 58: The method of example 57, further comprising applying an adhesive layer to an external surface of the encapsulating layer.

Example 59: The method of any of examples 51 through 58, wherein the inorganic particles are chosen from ZnO, TiO2, CeO2, and mixtures and combinations thereof.

Example 60: The method of any of examples 51 through 59, wherein the inorganic particles consist essentially of ZnO.

Example 61: A method for real-time monitoring of optical irradiance in situ on skin of a patient includes applying a skin-wearable photodetector module to the skin of the patient, the photodetector module includes an array includes an active layer between a metal anode and a metal cathode, wherein the active layer comprises a ternary mixture of a polymeric electron donor, a polymeric electron acceptor, and a charge carrier trap material; and monitoring, with the photodetector module, irradiance on the skin of the patient to diagnose or treat a medical condition.

Example 62: The method of example 61, wherein the monitoring comprises transmitting data from the photodetector module to a computing device.

Example 63: The method of example 62, further comprising storing the data in a database.

Example 64: The method of any of examples 61 through 63, wherein the monitoring comprises continuous monitoring for a period of at least 24 hours.

Example 65: A method for making a monitoring optical irradiance on a selected region of the skin of a patient includes selecting a plurality of optical filters for monitoring the irradiance over a desired wavelength range, wherein each optical filter of the plurality of optical filters comprises a central wavelength in a wavelength rage of about 100 nm to about 1000 nm; forming, with a three-dimensional (3D) extrusion process, a photodetector of a plurality of photodetectors over each optical filter of the plurality of optical filters, wherein the 3D extrusion process comprises extruding, for each photodetector of the plurality of photodetectors, a ternary mixture of a polymeric electron donor, a polymeric electron acceptor, and inorganic UV-absorbing nanoparticles onto an anode of the corresponding photodetector to form an active layer.

Example 66: The method of example 65, wherein the active layer comprises a ratio by weight, based on a total weight of the active layer, of: about 1.0 parts of polymeric electron donor:about 0.5 to about 1.2 parts of a polymeric primary electron acceptor:greater than about 0 parts and up to about 5 parts of inorganic particles.

Example 67: The method of any of examples 65 and 66, comprising forming the plurality of optical filters with 3D extrusion.

Example 68: The method of any of examples 65 through 67, further comprising encapsulating the plurality of photodetectors and the plurality of optical filters within an encapsulating layer to form a photodetector module.

Example 69: The method of example 68, further comprising applying an adhesive layer on an external surface of the encapsulating layer of the photodetector module.

Example 70: The method of example 69, further comprising adhering the photodetector module to the skin of the patient via the adhesive layer.

Example 71: The method of example 70, further comprising connecting the photodetector module to a control console, wherein the control console comprises a data processing module configured to monitor an output of the photodetector module.

Example 72: A photodetector includes an active layer includes about 1.0 parts of polymeric electron donor:about 0.5 parts to about 1.2 parts of a polymeric primary electron acceptor:greater than about 0 parts and up to about 3 parts of inorganic particles.

Example 73: A method for real-time monitoring of optical irradiance on a surface includes applying to the surface a skin-wearable photodetector module, the photodetector module includes an active layer between a metal anode and a metal cathode, wherein the active layer comprises a ternary mixture of a polymeric electron donor, a polymeric electron acceptor, and a charge carrier trap material; and monitoring, with the photodetector module, irradiance on the skin of the patient to diagnose or treat a medical condition.

Example 74: The method of example 73, wherein the monitoring comprises transmitting data from the photodetector module to a computing device.

Example 75: A photodetector module includes an array includes a substrate defining a first major surface and a second major surface, wherein the second major surface overlies a corresponding optical filter of the plurality of optical filters; an electrode overlying the first major surface of the substrate and defining an interior region; an anode within the interior region of the electrode; an active layer overlying the anode and comprising a ternary mixture of an electron donor, an electron acceptor, and at least one charge carrier trap material; and a cathode overlying the active layer; wherein the photodetector module is configured to be implanted in a human body.

Example 76: The photodetector module of example 75, wherein the plurality of photodetectors and the plurality of optical filters are encapsulated within an encapsulating layer of a polymer.

Example 77: The photodetector module of any of examples 75 and 76, wherein the charge carrier trap material in the active layer is chosen from inorganic ultraviolet (UV)-absorbing nanoparticles, quantum dots, organic dyes, and mixtures and combinations thereof.

Example 78: The photodetector module of any of examples 75 through 77, wherein the photodetector module is configured to be implanted in an orbit of a human cranium.

Example 79: The photodetector module of example 78, wherein the photodetector module comprises a replacement human eye.

Various examples have been described. These and other examples are within the scope of the following claims.

The invention claimed is:

1. A skin-wearable photodetector module, comprising:

an array comprising:

a plurality of photodetectors; and a plurality of optical filters, wherein each photodetector of the plurality of photodetectors is configured to receive an optical input from an environment via an optical filter of the plurality of optical filters having a central wavelength in a wavelength range of about 100 nm to about 1000 nm, and wherein each photodetector comprises:

a substrate defining a first major surface and a second major surface, wherein the second major surface overlies a corresponding optical filter of the plurality of optical filters;

an electrode overlying the first major surface of the substrate and defining an interior region;

an anode within the interior region of the electrode;

an active layer overlying the anode and comprising a ternary mixture of an electron donor, an electron acceptor, and at least one charge carrier trap material; and a cathode overlying the active layer.

2. The photodetector module of claim 1, wherein each of the photodetectors of the plurality of photodetectors and a corresponding optical filter of the plurality of optical filters are within an encapsulating layer of a polymer.

3. The photodetector module of claim 2, wherein an external surface of the encapsulating layer comprises an adhesive layer.

4. The photodetector module of claim 2, further comprising a connector circuit encapsulated in the encapsulating layer and electrically coupled to the electrode.

5. The photodetector module of claim 4, wherein the connector circuit comprises an arrangement of serpentine electrodes.

6. The photodetector module of claim 1, wherein the charge carrier trap material comprises inorganic UV-absorbing particles.

7. The photodetector module of claim 6, wherein the active layer comprises a ratio by weight, based on a total weight of the active layer, of: about 1.0 parts of polymeric electron donor:about 0.5 to about 1.5 parts of a polymeric electron acceptor:greater than about 0 parts and up to about 5 parts of inorganic UV-absorbing particles.

8. The photodetector module of claim 6, wherein the inorganic UV-absorbing particles comprise ZnO.

9. The photodetector module of claim 1, further comprising an insulating layer separating the anode and the cathode, wherein the insulating layer has a cylindrical shape, and wherein the insulating layer encircles the anode and the active layer within an interior region of the cylindrical insulating layer.

10. The photodetector module of claim 1, wherein each of the optical filters has a central wavelength that differs by about 50 nm to about 100 nm over the wavelength range.

11. The photodetector module of claim 1, wherein the module is sufficiently stretchable such that a photocurrent and a dark current produced by the module varies no more than about ±10 μA under a tensile strain of up to about 30%, wherein the module is sufficiently flexible such that a photocurrent produced by the module varies no more than about +10 μA at a curvature of up to about 1.5 $cm^{-1}$, and wherein the module has an external quantum efficiency (EQE) of greater than 10% at a wavelength range of 300-700 nm at a bias voltage of −1 V.

12. The photodetector module of claim 1, wherein the substrate comprises a polymeric material that is transparent to incident light with a wavelength of about 100 nm to about 1000 nm.

13. The photodetector module of claim 1, wherein the first major surface of the substrate comprises a modified surface, and wherein the modified surface has enhanced wettability to an anode material.

14. The photodetector module of claim 1, wherein the anode comprises a conducting or semiconducting polymer.

15. The photodetector module of claim 1, wherein the electron donor comprises a polythiophene, and wherein the electron acceptor comprises a functionalized fullerene.

16. The photodetector module of claim 1, wherein the cathode comprises EGaIn.

17. A photodetection system configured for removable attachment to human skin, the system comprising:

a skin-wearable photodetector module, comprising:

an array comprising a plurality of photodetectors and a plurality of optical filters, wherein each photodetector of the plurality of photodetectors is configured to receive an optical input from an environment via an optical filter of the plurality of optical filters having a central wavelength selected in a wavelength range of about 100 nm to about 1000 nm, and wherein each photodetector comprises:

a substrate defining a first major surface and a second major surface, wherein the substrate comprises a polymeric material that is transparent to incident light with a wavelength of about 100 nm to about 1000 nm, and wherein the second major surface of the substrate is adjacent to a corresponding optical filter of the plurality of optical filters;

a metal electrode overlying the first major surface of the substrate and comprising an interior region;

an anode overlying the first major surface of the substrate and the interior region of the metal electrode, wherein the anode comprises a conducting or semiconducting polymer;

a metal cathode; and an active layer between the anode and the metal cathode, wherein the active layer comprises a ternary mixture of a polymeric electron donor, a polymeric electron acceptor, and inorganic UV absorbing particles, and wherein the active layer comprises a ratio by weight, based on a total weight of the active layer, of:

about 1.0 parts of polymeric electron donor:about 0.5 parts to about 1.5 parts of a polymeric primary electron acceptor:greater than about 0 parts and up to about 5 parts of inorganic UV absorbing particles;

a connector circuit electrically coupled to the metal electrode; and an encapsulating layer encapsulating the plurality of photodetectors, the plurality of optical filters, and the connector circuit;

a connector electrically coupled to the connector circuit; and a control console connected to the connector circuit, wherein the control console comprises a signal processing module, a data processing module, and a power supply.

18. The photodetection system of claim 17, wherein the power supply comprises at least one of:

a battery configured to provide power sufficient to operate the photodetection system for at least 24 hours; or a solar cell.

19. The photodetection system of claim 17, wherein the inorganic particles consist essentially of ZnO, and wherein the active layer comprises the ratio by weight, based on the total weight of the active layer, of about 1.0 parts of a polymeric electron donor:about 0.8 parts of a polymeric electron acceptor:about 1.0 parts to about 2.5 parts of inorganic particles.

20. A method for real-time monitoring of optical irradiance in situ on skin of a patient, the method comprising:

applying a skin-wearable photodetector module to the skin of the patient, the photodetector module comprising:

an array comprising a plurality of photodetectors and a plurality of optical filters, wherein each photodetector in the array of the plurality of photodetectors is configured to receive an optical input from an environment via an optical filter of the plurality of optical filters having a central wavelength selected in a wavelength range of about 100 nm to about 1000 nm, and wherein each photodetector in the array of photodetectors comprises:

an active layer between a metal anode and a metal cathode, wherein the active layer comprises a ternary mixture of a polymeric electron donor, a polymeric electron acceptor, and a charge carrier trap material; and monitoring, with the photodetector module, irradiance on the skin of the patient to diagnose or treat a medical condition.

* * * * *